United States Patent
Suzuki et al.

(10) Patent No.: US 7,858,348 B2
(45) Date of Patent: Dec. 28, 2010

(54) N-ACETYL-(R,S)-BETA-AMINO ACID ACYLASE GENE

(75) Inventors: Shunichi Suzuki, Kawasaki (JP); Yuki Imabayashi, Kawasaki (JP); Kunihiko Watanabe, Kawasaki (JP); Hisashi Kawasaki, Yokohana (JP); Tsuyoshi Nakamatsu, Yokohama (JP)

(73) Assignee: Ajinomoto Co., Inc., Tokyo (JP)

( * ) Notice: Subject to any disclaimer, the term of this patent is extended or adjusted under 35 U.S.C. 154(b) by 585 days.

(21) Appl. No.: 11/782,260

(22) Filed: Jul. 24, 2007

(65) Prior Publication Data

US 2008/0241895 A1    Oct. 2, 2008

(30) Foreign Application Priority Data

Jul. 26, 2006   (JP) .............................. 2006-202836

(51) Int. Cl.
*C12P 13/04* (2006.01)
(52) U.S. Cl. ........................ 435/106; 435/228; 536/23.2
(58) Field of Classification Search ................. 435/106, 435/228; 536/23.2

See application file for complete search history.

(56) References Cited

PUBLICATIONS

Sequence comparison between SEQ ID No. 10 and Accession No. B1G3Y5 (2008).*

* cited by examiner

*Primary Examiner*—Tekchand Saidha
(74) *Attorney, Agent, or Firm*—Shelly Guest Cermak; Cermak Nakajima LLP

(57) ABSTRACT

The present invention provides genes that encode the N-acetyl-(R,S)-β-amino acid acylases. The N-acetyl-(R,S)-β-amino acid acylases were isolated and purified from bacterial cells and the nucleotide sequences were determined. A host, such as *Escherichia coli*, was used to construct a high-expression system for these genes. The N-acetyl-(R)-β-amino acid acylase produced by *Burkholderia* sp. AJ110349 (FERM BP-10366) includes, for example, the protein having the amino acid sequence shown in SEQ. ID. NO. 8. The gene encoding this enzyme includes, for example, the DNA having the nucleotide sequence as shown in SEQ. ID. NO. 7. The N-acetyl-(S)-β-amino acid acylase produced by *Burkholderia* sp. AJ110349 (FERM BP-10366) includes, for example, the protein having the amino acid sequence shown in SEQ. ID. NO. 10. The gene encoding this enzyme includes, for example, the DNA having the nucleotide sequence shown inshown in SEQ. ID. NO. 9. The N-acetyl-(R)-β-amino acid acylase produced by *Variovorax* sp. AJ110348 (FERM BP-10367) includes, for example, the protein comprised of the amino acid sequence shown in SEQ. ID. NO. 12. The gene encoding this enzyme includes, for example, the DNA having the nucleotide sequence shown inshown in SEQ. ID. NO. 11.

4 Claims, 2 Drawing Sheets

US 7,858,348 B2

N-ACETYL-(R,S)-BETA-AMINO ACID ACYLASE GENE

This application claims priority under 35 U.S.C. §119 to Japanese Patent Application No. 2006-202836, filed Jul. 26, 2006, which is incorporated by reference. The Sequence Listing filed electronically herewith is also hereby incorporated by reference in its entirety (File Name: US-343_Seq_List_Copy__1; File Size: 45 KB; Date Created: Jul. 24, 2007).

BACKGROUND OF THE INVENTION

1. Field of the Invention

The present invention relates to a new N-acetyl-(R)-β-amino acid acylase, a new N-acetyl-(S)-β-amino acid acylase, genes encoding them, and methods for their use.

2. Brief Description of the Related Art

Enzymes having acylase activity on N-acetyl-β-amino acids have not been previously reported. The present inventors were the first to discover the bacterial strains of *Variovorax* sp. AJ110348 (FERM BP-10367) and *Burkholderia* sp. AJ110349 (FERM BP-10366), which are able to optically selectively deacetylate.

N-acetyl-β-amino acids such as N-acetyl-β-phenylalanine are produced by using bacterial cells of the above bacterial strains. A method for optically selectively deacetylating such bacterial cells or the supernatant of ruptured bacterial cells are described in Japanese Patent Application Publication No. 2006-42722. These bacterial strains were deposited in an international depository on Jul. 4, 2005, under the Budapest Treaty on the International Recognition of the Deposit of Microorganisms for the Purposes of Patent Procedure. These strains were derived from FERM P-20129 and FERM P-20128, which were deposited with the International Patent Organism Depositary (an independent administrative institution) of the National Institute of Advanced Industrial Science and Technology on Jul. 22, 2004.

SUMMARY OF THE INVENTION

In wild-type strains, it is difficult to select for the N-acetyl-β-amino acid acylase derived from *Burkholderia* sp. AJ110349 because this strain acts on both the (R) and (S) forms. Therefore, it is difficult to selectively produce β-amino acids using these wild-type strains. To achieve a more efficient conversion, it is desirable to isolate and identify enzymes that catalyze the reaction, identify the genes encoding these enzymes, and construct a high-expression system using *Escherichia coli* as host.

As set forth herein, the present invention was devised as a result of strenuous effort. It is an object of the present invention to provide a gene encoding a protein selected from the group consisting of:

(a) a protein comprising the amino acid sequence shown in SEQ. ID. NO. 8;

(b) a protein having N-acetyl-(R)-β-amino acid acylase activity, wherein said protein comprises the amino acid sequence shown in SEQ. ID. NO. 8 except there are one or more amino acid substitutions, deletions, or additions; and (c) a protein having N-acetyl-(R)-β-amino acid acylase activity, wherein the amino acid sequence of said protein has 70 percent or greater sequence homology with the amino acid sequence of SEQ. ID. NO. 8.

It is a further object of the present invention to provide a gene comprising a DNA selected from the group consisting of:

(a) DNA comprising the nucleotide sequence shown in SEQ. ID. NO. 7;

(b) DNA encoding a protein having N-acetyl-(R)-β-amino acid acylase activity, wherein said DNA is able to hybridize under stringent conditions with a DNA which is complementary to the nucleotide sequence shown in SEQ. ID. NO. 7; and (c) DNA encoding a protein having N-acetyl-(R)-β-amino acid acylase activity, wherein the DNA has 70 percent or greater sequence homology with the nucleotide sequence shown in SEQ. ID. NO. 7.

It is a further object of the present invention to provide a gene encoding a protein selected from the group consisting of:

(a) a protein comprising the amino acid sequence shown in SEQ. ID. NO. 10;

(b) a protein having N-acetyl-(S)-β-amino acid acylase activity, wherein said protein comprises the amino acid sequence shown in SEQ. ID. NO. 10, except there are one or more amino acid substitutions, deletions, or additions; and (c) a protein having N-acetyl-(S)-β-amino acid acylase activity, wherein the amino acid sequence of said protein has 70 percent or greater sequence homology with the amino acid sequence of SEQ. ID. NO. 10.

It is a further object of the present invention to provide A gene comprising a DNA selected from the group consisting of:

(a) DNA comprising the nucleotide sequence shown in SEQ. ID. NO. 9;

(b) DNA encoding a protein having N-acetyl-(S)-β-amino acid acylase activity, wherein said DNA is able to hybridize under stringent conditions with a DNA which is complementary to the nucleotide sequence shown in SEQ. ID. NO. 9; and (c) DNA encoding a protein having N-acetyl-(S)-β-amino acid acylase activity, wherein the DNA has 70 percent or greater sequence homology with the nucleotide sequence shown in SEQ. ID. NO. 9.

It is a further object of the present invention to provide A gene encoding a protein selected from the group consisting of:

(a) a protein comprising the amino acid sequence shown in SEQ. ID. NO. 12;

(b) a protein having N-acetyl-(R)-β-amino acid acylase activity, wherein said protein comprises the amino acid sequence shown in SEQ. ID. NO. 12, except there are one or more amino acid substitutions, deletions, or additions; and (c) a protein having N-acetyl-(R)-β-amino acid acylase activity, wherein the amino acid sequence of the protein has 70 percent or greater sequence homology with the amino acid sequence of SEQ. ID. NO. 12.

It is a further object of the present invention to provide a gene comprising a DNA selected from the group consisting of:

(a) DNA comprising the nucleotide sequence shown in SEQ. ID. NO. 11;

(b) DNA encoding a protein having N-acetyl-(R)-β-amino acid acylase activity, wherein said DNA is able to hybridize under stringent conditions with a DNA which is complementary to the nucleotide sequence shown in SEQ. ID. NO. 11; and (c) DNA encoding a protein having N-acetyl-(R)-β-amino acid acylase activity, wherein the DNA has 70 percent or greater sequence homology with the nucleotide sequence shown in SEQ. ID. NO. 11.

It is a further object of the present invention to provide the gene as described above wherein said acylase acts on a N-acetyl-β-amino acid selected from the group consisting of N-acetyl-β-phenylalanine, N-acetyl-β-leucine, N-acetyl-β- homoleucine, N-acetyl-β-homophenylalanine, N-acetyl-β-tyrosine, N-acetyl-β-4-fluorophenylalanine, N-acetyl-β-aminobutyric acid, 3,4-(-0-CH2-0-)-N-acetyl-β-phenylalanine, N-acetyl-β-3-Pyridylalanie, and combinations thereof.

It is a further object of the invention to provide a protein selected from the group consisting of:

(a) a protein comprising the amino acid sequence shown in SEQ. ID. NO. 8;

(b) a protein having N-acetyl-(R)-β-amino acid acylase activity, wherein said protein comprises the amino acid sequence shown in SEQ. ID. NO. 8, except there are one or more amino acid substitutions, deletions, or additions; and (c) a protein having N-acetyl-(R)-β-amino acid acylase activity, wherein the amino acid sequence of said protein has 70 percent or greater sequence homology with the amino acid sequence of SEQ. ID. NO. 8.

It is a further object of the present invention to provide a protein selected from the group consisting of:

(a) a protein comprising the amino acid sequence shown in SEQ. ID. NO. 10;

(b) a protein having N-acetyl-(S)-β-amino acid acylase activity, wherein said protein comprises the amino acid sequence shown in SEQ. ID. NO. 10, except there are one or more amino acid substitutions, deletions, or additions; and (c) a protein having N-acetyl-(S)-β-amino acid acylase activity, wherein the amino acid sequence of said protein has 70 percent or greater sequence homology with the amino acid sequence of SEQ. ID. NO. 10.

It is a further object of the present invention to provide a protein selected from the group consisting of:

(a) a protein comprising the amino acid sequence shown in SEQ. ID. NO. 12;

(b) a protein having N-acetyl-(R)-β-amino acid acylase activity, wherein said protein comprises the amino acid sequence shown in SEQ. ID. NO. 12, except there are one or more amino acid substitutions, deletions, or additions; and (c) a protein having N-acetyl-(R)-β-amino acid acylase activity, wherein the amino acid sequence of said protein has 70 percent or greater sequence homology with the amino acid sequence of SEQ. ID. NO. 12.

It is a further object of the present invention to provide the acylase as described above, wherein said acylase acts on a N-acetyl-β-amino acid selected from the group consisting of N-acetyl-β-phenylalanine, N-acetyl-β-leucine, N-acetyl-β-homoleucine, N-acetyl-β-homophenylalanine, N-acetyl-β-tyrosine, N-acetyl-β-4-fluorophenylalanine, N-acetyl-β-aminobutyric acid, 3,4-(-0-CH2-0-)-N-acetyl-β-phenylalanine, and N-acetyl-β-3-pyridylalanine.

It is a further object of the present invention to provide a microorganism transformed by the gene as described above.

It is a further object of the present invention to provide Escherichia coli transformed by the gene as described above.

It is a further object of the present invention to provide a method for manufacturing β-amino acids comprising contacting the microorganism described above with N-acetyl-β-amino acid, inducing the production of one or more β-amino acids, and recovering the β-amino acids.

It is a further object of the present invention to provide a method for manufacturing β-amino acids comprising contacting a protein having N-acetyl-β-amino acid acylase activity obtained from the microorganism as described above with N-acetyl-β-amino acid, inducing the production of one or more β-amino acids, and recovering the β-amino acids. Based on the present invention, N-acetyl-(R)-β-amino acid acylase and N-acetyl-(S)-β-amino acid acylase have been isolated and identified, their genes have been cloned, and their nucleotide sequences and the amino acid sequences of the proteins encoded by these genes have been elucidated.

DETAILED DESCRIPTION OF THE PREFERRED EMBODIMENTS

Figure 1:
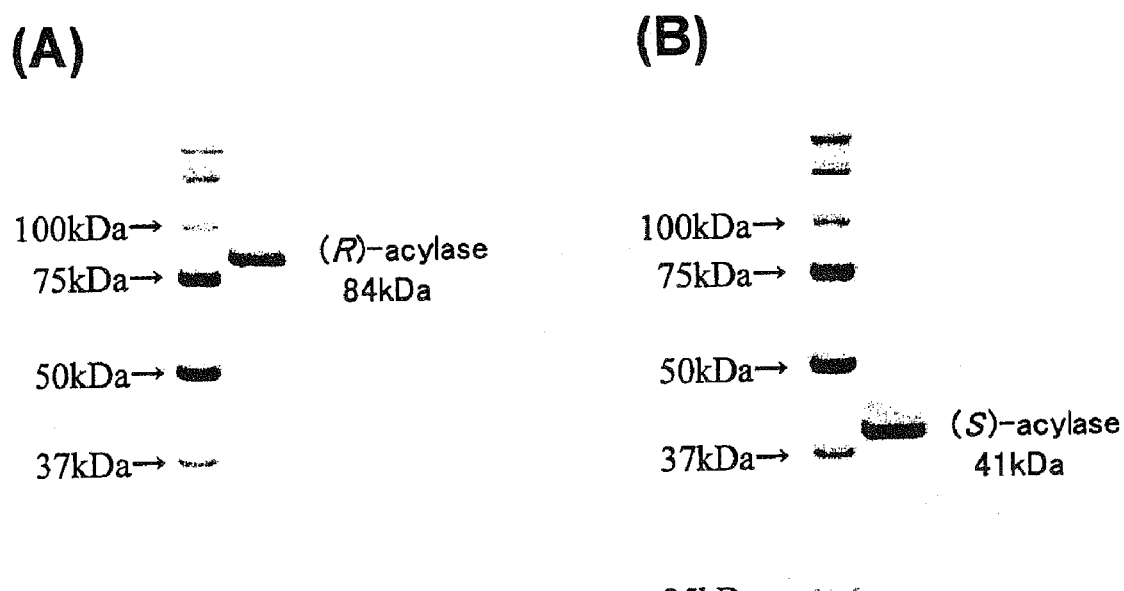
FIG. 1: The results of observation by SDS-PAGE of (A) purified N-acetyl-(R)-β-amino acid acylase and (B) N-acetyl-(S)-β-amino acid acylase.

Numerous methods of isolating and identifying enzymes that support the activity of bacterial strains found to have enzymatic activity have been reported. Specifically, these include gene isolation by shotgun cloning, and isolating an enzyme, determining the amino acid sequence of a particular portion, and isolating the gene based on the sequence information.

Accordingly, the present inventors first attempted to employ the usual method of shotgun cloning to obtain the N-acetyl-β-amino acid acylase that deacetylates N-acetyl-β-amino acids in an optically selective manner from the bacterial strains described in Japanese Patent Application Publication No. 2006-42722.

A genomic DNA library was created from Burkholderia sp. AJ110349, and was coated on a medium having as a sole carbon source N-acetyl-R/S-β-Phe. Culturing was conducted at 37° C. for one week.

The number of donor specimens was determined by separately coating the library on LB medium and calculating the number of bacterial cells that grew on the LB medium. Screening of about 10,000 bacterial strains yielded no strains that grew using N-acetyl-R/S-β-Phe as the sole carbon source.

Similarly, about 51,000 strains of Variovorax sp. AJ110348 were screened to find those that are able to utilize N-acetyl-R/S-β-Phe as the sole carbon source. However, in the same manner as when screening strains of Burkholderia sp. AJ110349, no strain that grew using N-acetyl-R/S-β-Phe as its sole carbon source was obtained.

As set forth above, although an extremely large number of clones were examined, screening using a sole carbon source as the indicator did not yield the desired enzyme gene.

Thus, the second approach of isolating and purifying the enzyme was attempted. Numerous methods of isolating and purifying enzymes have been reported. However, when isolating and purifying proteins there are no general principles that guarantee the isolation and purification of every possible protein. Furthermore, the level of difficulty of isolation and purification varies greatly depending on the ratio of the targeted protein to the total quantity of protein present in the bacteria. The method of purifying N-acetyl-β-amino acid acylase employed in the present invention is described in detail further below. When purifying N-acetyl-(R)-β-amino acid acylase and N-acetyl-(S)-β-amino acid acylase from Burkholderia sp. AJ110349, the isolated and purified enzyme has a specific activity that is several hundred times that of the target enzyme in a cell-free extract. This purification proved to be extremely difficult. One of the reasons for this difficulty was that the cells of Burkholderia sp. AJ110349, the bacterium that produces the enzyme, often fail to concentrate when centrifuged. When isolating and purifying a protein within cells, a buffer solution is normally employed to thoroughly clean the cells, once the cells have been concentrated so as to prevent the protein from mixing into the medium. This strain tends not to be recoverable in pellet form when concentrated by typical centrifugal separation methods, and it is difficult to separate proteins derived from the medium components from proteins derived from the cells. Thus, the isolation and purification of protein from this strain requires isolation from a state in which many undesired proteins are present than is normally the case, which is one reason for the difficulty in purification.

To solve this problem, the present inventors conducted extensive research into a great number of purification conditions than is normally the case for protein purification. This resulted in the discovery that five types of chromatography were necessary to successfully isolate and purify the above enzyme, which is an unexpected number even for persons skilled in the art. As a result, the nucleotide sequence of the gene encoding the above enzyme was determined.

Furthermore, since it was not necessary to separately obtain several enzymes for Variovorax sp. AJ110348, the procedure was improved and shotgun cloning was continued. Since the enzyme gene had not been obtained by simple screening in which strains having the target gene were selectively grown as set forth above, the present inventors, as will be described further below, conducted an extremely time-consuming operation in which the activity of each clone was separately determined to successfully obtain the gene for the targeted enzyme.

The Genes of the Present Invention

The genes of the present invention encode N-acetyl-(R)-β-amino acid acylase and N-acetyl-(S)-β-amino acid acylase. These enzymes have homodimer and homotrimer structures which include subunits (structural units) having molecular weights of about 84 kDa and 41 kDa, respectively. Accordingly, and more specifically, the genes of the present invention encode the polypeptides that are the various subunits of these enzymes. Burkholderia sp. AJ110349 (FERM BP-10366) produces typical examples of these enzymes. Specific examples of the amino acid sequences thereof are given by SEQ. ID. NOS. 8 and 10. Further typical examples of these enzymes are produced by Variovorax sp. AJ110348 (FERM BP-10367). A specific example of the amino acid sequence thereof is SEQ. ID. NO. 12. A typical example of an N-acetyl-(R,S)-β-amino acid acylase in the present invention is N-acetyl-(R,S)-β-phenylalanine (Phe) acylase. Whether N-acetyl-(R,S)-β-amino acid acylase has R-form specific activity or S-form specific activity is determined using N-acetyl-(R,S)-β-phenylalanine acylase as the substrate. Similar to the recognition of the D-form and L-form of α-amino acids, the N-acetyl-(R,S)-β-amino acid acylase of the present invention, recognizes the corresponding positions of hydrogen, carboxyl groups, amino groups, and side chains. In the RS notation, precedence based on the cis-position and —C—COOH are sometimes interchangable based on the side chain that is bound at the β-position. For example, in the embodiments described further below, the S-form is produced from N-acetyl-(R)-β-amino acid acylase in the case of N-acetyl-β-homoLeu and the R-form is produced from N-acetyl-(S)-β-amino acid acylase in the case of N-acetyl-β-homoPhe.

A "protein having N-acetyl-(R)-β-amino acid acylase activity or N-acetyl-(S)-β-amino acid acylase activity" means a protein (or polypeptide) which has structural units (or functional structural units) of various acylase enzymes having a homodimer or homotrimer structure.

The genes of the present invention can be prepared by methods known to those skilled in the art.

For example, according to the method described in the embodiments of the present specification, in addition to colony hybridization using various probes, the genomic DNA of Burkholderia sp. AJ110349 (FERM BP-10366) or Variovorax sp. AJ110348 (FERM BP-10367) can be employed as the DNA template, and a primer that has been suitably prepared based on information relating to the amino acid sequence or the nucleotide sequence of the DNA of the present invention can be employed to prepare the genes of the present invention by amplification by any form of PCR known to those skilled in the art.

For example, a PCR of 2 minutes at 94° C., 30 cycles of 10 seconds at 94° C., 20 seconds at 55° C., and 2 minutes at 72° C. can be conducted, followed by 5 minutes at 72° C. A common thermal cycler, such as a Perkins-Elmer Model 9600, can be employed. A common commercial heat-resistant DNA polymerase, such as ExTaq DNA Polymerase (made by Takara Shuzo), can be employed, and the composition of the reaction solution can be determined according to the instruction manual provided with the polymerase.

The various genes of the present invention can be prepared by methods of chemical synthesis known to those skilled in the art.

In the present specification, the term "under stringent conditions" means conditions under which specific hybrids form but nonspecific hybrids do not. As an example, these are conditions under which two strands of DNA having a high degree of homology (for example, DNA strands having 50 percent or greater, desirably 70 percent or greater, preferably 80 percent or greater, more preferably 90 percent or greater, and still more preferably, 95 percent or greater homology) hybridize, but two strands of DNA of lower homology do not hybridize. Homology between nucleotide sequences can be determined by algorithms known to those in the art, such as the Blast algorithm. As a more specific example, these are conditions under which hybridization occurs at salt concentrations corresponding to 60° C., 1×SSC, 0.1 percent SDS, preferably 0.1×SSC and 0.1 percent SDS, which are the normal Southern hybridization washing conditions. DNA strands that hybridize under such conditions include those having stop codons part way through and those that have lost their activity due to a mutation in the activity center. However, in such DNA strands, the N-acetyl-(R)-β-amino acid acylase or N-acetyl-(S)-β-amino acid acylase activity can be detected and eliminated by the method described further below.

Hybridization can be conducted by the method described in Current Protocols in Molecular Biology (edited by Frederick M. Ausubel et al., 1987), methods known to those skilled in the art, and methods based on such methods. It can also be conducted by methods described in commercial DVDs and accompanying instruction manuals.

The Proteins of the Present Invention

The proteins encoded by the genes of the present invention are proteins having the amino acid sequences (SEQ. ID. NO. 8, 10, or 12) of the unit polypeptides constituting N-acetyl-(R)-β-amino acid acylase or N-acetyl-(S)-β-amino acid acylase with one or more amino acid residue substitutions, deletions, or additions. Proteins having the above-described enzymatic activity can be readily prepared by suitable combinations of any of the methods known to those skilled in the art, such as the introduction of site-specific mutations, homologous recombination, primer extension, and PCR methods.

In this process, since they have substantially equivalent functions, the possibility of substituting amino acids within the same family (polar and β-nonpolar amino acids, hydrophobic and β-hydrophilic amino acids, positive and β-negative charge amino acids, aromatic amino acids, and the like) among the amino acids that constitute a particular polypeptide is also conceivable. To maintain essentially equivalent functioning, the amino acids within the functional domains contained in the various polypeptides of the present invention are desirably retained.

Further examples of the proteins of the present invention are proteins, or fragments thereof, containing amino acid sequences having a high degree of sequence homology, averaging about 70 percent overall, desirably about 80 percent or more, preferably about 90 percent or more, and more preferably, 95 percent or more, with the above amino acid sequences, that have the N-acetyl-(R)-β-amino acid acylase or N-acetyl-(S)-β-amino acid acylase activity. Homology between amino acid sequences can also be determined by algorithms known to those skilled in the trade, such as the Blast method employed in the embodiments. The above enzymatic activity can be measured by the method described in the embodiments of the present specification. Such proteins can also be readily prepared by suitable combinations of any of the methods known to those skilled in the art, such as the introduction of site-specific mutations, homologous recombination, primer extension, and PCR methods.

Expression of the Genes of the Present Invention

The genes of the present invention obtained as set forth above can be incorporated into recombination vectors by any of the methods known to those skilled in the art to create the recombination expression vectors.

For example, (1) a DNA fragment containing the gene of the present invention can be excised, (2) inserted at a restrictase site or muticloning site in a suitable recombination vector, and ligated to the vector to prepare a recombination expression vector. The recombination vector is not specifically limited. For example, recombination vectors in the form of plasmids derived from *Aspergillus nidulans* (such as pSal23, pTAex3, pNGU113, pRBG1, pGM32, pSE52, and pNAGL142), plasmids derived from *Escherichia coli* (such as pT7Blue T-Vector, pRSET, pBR322, pBR325, pUC18, and pUC118), plasmids derived from *Bacillus subtilis* (such as pUB110, pTP5, and pC194), and plasmids derived from yeast (such as pSH19 and pSH15) can be employed.

In addition to the above, so long as the activity of the transcription-regulating sequence of the present invention is not lost, various promoter transcription-regulating elements, Shine Delgarno sequences, selection markers, transcription termination signals, and the like known in this field of art can be added as desired to the above recombination vector. As needed, the targeted proteins encoded by the external genes of the present invention can be expressed as fused genes with other proteins or peptides (such as glutathione-S-transferase, histidine tags, calmodulin-binding proteins, and protein A). Such fused proteins can be cleaved with suitable proteases and separated into independent proteins.

So long as the genes of the present invention are effectively expressed, neither the type or derivation of the host employed to prepare a microbe (transformant) having the recombination expression vector of the present invention are specifically limited. For example, any microbial cell known to those skilled in the art, such as a prokaryotic cell such as *Escherichia coli* or a eukaryotic cell such as *Saccharomyces cerevisiae* (brewer's yeast), can be employed.

The host cell can be transformed by a method known in the art, such as the calcium chloride method, use of a particle gun, or the electroporation method. For example, the following literature may be consulted: Proc. Natl. Acad. Sci. USA, Vol. 69, 2110 (1972); Gene, Vol. 17, 107 (1982); Molecular and General Genetics, Vol. 168, 111 (1979); Methods in Enzymology, Vol. 194, 182-187 (1991); Proc. Natl. Acad. Sci. USA, Vol. 75, 1929 (1978); Cell Engineering, Vol. 8, New Cell Engineering Experiment Protocols, 263-267 (1995) (pub. by Shujunsha); and Virology, Vol. 52, 456 (1973).

The transformant of the present invention thus obtained can be cultured by a method known to those skilled in the art.

In the course of preparing a protein in the present invention, a method known to those skilled in the art can be suitably selected. For example, methods known to those skilled in the art, such as the use of various chromatographic columns, filters, ultrafiltration, salting out, solvent precipitation, solvent extraction, distillation, immunoprecipitation, SDS-polyacrylamide gel electrophoresis, isoelectric focusing electrophoresis, dialysis, and crystallization, can be suitably selected and combined to separate and purify the protein in essentially pure and uniform form.

When expressing the protein as a fused protein with glutathione-S-transferase or as a recombinant protein to which multiple histidines are attached, the recombinant protein that is expressed can be purified using a glutathione column or nickel column. Following purification of a fused protein, as needed, the regions outside the target protein can be cut away and eliminated with thrombin, factor Xa, or the like. Alternatively, a suitable protein modifying enzyme such as trypsin, chymotrypsin, lysyl endopeptidase, protein kinase, or glucosidase can be used to treat the protein, either before or after purification, to modify the protein or partially remove a peptide.

The present invention provides a method for manufacturing β-amino acids by contacting a microbe that has been transformed with a gene encoding a protein having N-acetyl-β-amino acid acylase activity with an N-acetyl-β-amino acid, inducing the production of the β-amino acid, and recovering the β-amino acid. The present invention also provides a method for manufacturing β-amino acids, characterized by contacting a protein having N-acetyl-β-amino acid acylase activity obtained from this microbe with an N-acetyl-β-amino acid, inducing the production of the β-amino acid, and recovering the β-amino acid.

The β-amino acid of the present invention is shown below:

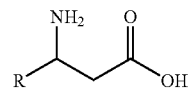

R denotes a group selected from among alkyl groups having 1 to 6 carbon atoms, aryl groups having 6 to 14 carbon atoms, cycloalkyl groups having 3 to 10 carbon atoms, aralkyl groups having 7 to 19 carbon atoms, alkoxyalkyl groups having 2 to 11 carbon atoms, groups having a hetero atom on one of these carbon skeletons, and groups comprising a carbon-carbon unsaturated bond on one of these carbon skeletons, it being permissible for the group to be either linear or branched, and to be optionally further substituted. Desirably, R denotes an alkyl group having 1 to 4 carbon atoms, or an aryl group having 6 or 7 carbon atoms, that is either linear or branched, and optionally further substituted. It is desirable to select the β-amino acid from among β-phenylalanine, β-leucine, β-homoleucine, β-homophenylalanine, β-tyrosine, β-4-fluorophenylalanine, β-aminobutyric acid, 3,4-(-0-CH2-0-)-β-phenylalanine, and β-Pyridylalanine.

In the manufacturing methods of the present invention, any of the types, methods, conditions, and the like for exerting the effects of various acylases known to those skilled in the art may be suitably selected based on various conditions such as the type and quantity of N-acetyl-β-amino acid, the type of acylase, and the scale of manufacturing.

For example, N-acetyl-β-amino acid can be added to a suspension of the bacterial cells of the present invention, or N-acetyl-β-amino acid can be added to the supernatant of a solution of ruptured bacterial cells, to cause the acylase to exert its effect.

The reaction temperature is desirably 10 to 60° C., preferably 20 to 40° C. The pH of the reaction system is desirably 4 to 10, preferably 6 to 9. The reaction time is 10 minutes to 120 hours, desirably 1 to 60 hours, preferably 1 to 48 hours. The reaction solvent may be in the form of an aqueous solution, MeOH, DMF, DMSO, or the like, or a mixture thereof may be employed.

EXAMPLES

The present invention is described in greater detail below. However, the technical scope of the present invention is not limited thereto.

1. Reagents (R,S)-β-Phe(DL-3-amino-3-phenylpropionic acid) was purchased from Sigma Aldrich Corp. (R)-β-Phe and (S)-β-Phe were purchased from Watanabe Chemicals. The other β-amino acids were purchased from the following manufacturers.

(R,S)-β-Leu
(DL-β-Leucine, Fluka Co.)
(R)-β-Leu
(L-β-Leucine Hydrochloride, Fluka Co.)
(R,S)-β-homoPhe
(DL-β-Homophenylalanine, Fluka Co.)
(S)-β-homoPhe
(L-β-Homophenylalanine Hydrochloride, Fluka Co.)
(R,S)-β-homoLeu
(3-Amino-5-methyl-hexanoic acid, Astatech, Inc.)
(R)-β-homoLeu
((R)-3-amino-5-methyl-hexanoic acid, Astatech, Inc.)
(R,S)-β-Tyr
(3-Amino-3-(4-hydroxyphenyl)-propanoic acid, Bionet Building Blocks Co.)
(R)-β-Tyr
((R)-3-Amino-3-(4-hydroxyphenyl)-propanoic acid, Peptech Co.)
(R,S)-4-Fluoro-β-Phe
(3-Amino-3-(4-fluorophenyl)-propanoic acid, Bionet Building Blocks Co.)
(R)-4-Fluoro-β-Phe
((R)-3-Amino-3-(4-fluorophenyl)-propanoic acid, Peptech Co.)
(R,S)-β-3-Pyr-Ala
(3-Amino-3-(3-pyridyl)-propanoic acid, Bachem Co.)

2. Synthesis

Various N-acetyl-β-amino acids were synthesized: racemic forms were synthesized by acetylating racemic β-amino acids and optically active forms were synthesized by acetylating optically active β-amino acids.

2-1. Synthesis of N-acetyl-(R,S)-β-Phe (R,S)-β-Phe (50 g, 303 mmol) was suspended in 200 mL of water, and a 25 percent NaOH aqueous solution was added and cooled with ice, and the pH was adjusted to a range of 11 to 12. While maintaining the pH of the aqueous solution within the range of 11 to 12 by adjusting the pH with 25 percent NaOH aqueous solution, acetic anhydride (62.8 mL, 664 mmol) was added drop-by-drop at room temperature with a dropping funnel. The mixture was stirred overnight, at which time analysis of the reaction mixture revealed the residual presence of the starting material, so more acetic anhydride (6 mL, 63 mmol) was added. The reaction mixture was filtered to remove insoluble material, concentrated hydrochloric acid was added to the filtrate, and the pH was adjusted to 2, causing crystals to precipitate out. The crystals were filtered out, washed with water, and dried overnight at 60° C. under reduced pressure, yielding N-acetyl-(R,S)-β-Phe (56.9 g, 274.3 mmol, 91 percent).

2-2. Synthesis of N-acetyl-(S)-β-Phe (S)-β-Phe (250 mg, 1.51 mmol) was suspended in 5 mL of water, 20 percent NaOH aqueous solution was added and cooled with ice, and the pH was adjusted to a range of 11 to 12. While maintaining the pH of the aqueous solution within the range of 11 to 12 by adjusting the pH with 20 percent NaOH aqueous solution, acetic anhydride (0.33 mL, 3.49 mmol) was added drop-by-drop at room temperature. The reaction mixture was filtered to remove insoluble material, concentrated hydrochloric acid was added to the solution, and the pH was adjusted to 2, causing crystals to precipitate out. The crystals were filtered out, washed with water, and dried overnight at 50° C. under reduced pressure, yielding N-acetyl-(S)-β-Phe (238 mg, 1.15 mmol, 76 percent).

2-3. Synthesis of N-acetyl-(R)-β-Phe (R)-β-Phe hydrochloride (250 mg, 1.24 mmol) was suspended in 5 mL of water, 20 percent NaOH aqueous solution was added and cooled with ice, and the pH was adjusted to a range of 11 to 12. While maintaining the pH of the aqueous solution within the range of 11 to 12 by adjusting the pH with 20 percent NaOH aqueous solution, acetic anhydride (0.28 mL, 2.96 mmol) was added dropwise at room temperature. The reaction mixture was filtered to remove insoluble material, concentrated hydrochloric acid was added to the solution, and the pH was adjusted to 2, causing crystals to precipitate out. The crystals were filtered out, washed with water, and dried overnight at 50° C. under reduced pressure, yielding N-acetyl-(R)-β-Phe (236 mg, 1.13 mmol, 91 percent).

2-4. Synthesis of N-acetyl-(R,S)-β-Leu (R,S)-β-Leu (995 mg, 7.58 mmol) was suspended in 8 mL of water, 20 percent NaOH aqueous solution was added, and the pH was adjusted to a range of 11 to 12. While maintaining the pH of the aqueous solution within the range of 11 to 12 by adjusting the pH with 20 percent NaOH aqueous solution, acetic anhydride (1.3 mL 13.3 mmol) was added drop-by-drop at room temperature. The reaction mixture was filtered to remove insoluble material, concentrated hydrochloric acid was added to the filtrate, and the pH was adjusted to 2, causing crystals to precipitate out. The crystals were filtered out, washed with water, and dried overnight at 50° C. under reduced pressure, yielding N-acetyl-(R,S)-β-Leu (382 mg, 2.21 mmol, 29.0 percent).

ESI-MS [M-H]=172

2-5. Synthesis of N-acetyl-(R,S)-β-homoPhe (R,S)-β-HomoPhe (198 mg, 1.12 mmol) was suspended in 5 mL of water, 20 percent NaOH aqueous solution was added, and the pH was adjusted to a range of 11 to 12. While maintaining the pH of the aqueous solution within the range of 11 to 12 by adjusting the pH with 20 percent NaOH aqueous solution, acetic anhydride (0.24 mL, 2.46 mmol) was added dropwise at room temperature. The reaction mixture was filtered to remove insoluble material, concentrated hydrochloric acid was added to the solution, and the pH was adjusted to 2, causing crystals to precipitate out. The crystals were filtered out, washed with water, and dried overnight at 50° C. under reduced pressure, yielding N-acetyl-(R,S)-β-homoPhe (64.5 mg, 0.36 mmol, 32.1 percent).

ESI-MS [M-H]=220

2-6. Synthesis of N-acetyl-(R,S)-β-homoLeu (R,S)-β-homoLeu (1.01 g, 6.9 mmol) was suspended in 16 mL of water, 20 percent NaOH aqueous solution was added, and the pH was adjusted to a range of 11 to 12. While maintaining the pH of the aqueous solution within the range of 11 to 12 by adjusting the pH with 20 percent NaOH aqueous solution, acetic anhydride (1.35 mL, 13.8 mmol) was added dropwise at room temperature. The reaction mixture was filtered to remove insoluble material, concentrated hydrochloric acid was added to the solution, and the pH was adjusted to 2, causing crystals to precipitate out. The crystals were filtered out, washed with water, and dried overnight at 50° C. under reduced pressure, yielding N-acetyl-(R,S)-β-homoLeu (64.5 mg, 5.07 mmol, 73.1 percent). This product was dissolved and solidified by drying under reduced pressure. NMR was used to confirm that the desired product had indeed been produced. The product was employed in the reaction without modification.

ESI-MS [M-H]=186

2-7. Synthesis of N-acetyl-(R,S)-β-Tyr (R,S)-β-Tyr (202 mg, 1.16 mmol) was suspended in 16 HL of water, 20 percent NaOH aqueous solution was added, and the pH was adjusted to a range of 11 to 12. While maintaining the pH of the aqueous solution within the range of 11 to 12 by adjusting the pH with 20 percent NaOH aqueous solution, acetic anhydride (0.33 mL, 3.39 mmol) was added drop-by-drop at room temperature. The reaction mixture was filtered to remove insoluble material, concentrated hydrochloric acid was added to the solution, the pH was adjusted to 2, and the solution was concentrated in an evaporator, causing crystals to precipitate out. The crystals were filtered out, washed with water, and dried overnight at 50° C. under reduced pressure, yielding N-acetyl-(R,S)-β-Tyr (55.5 mg, 0.25 mmol), 21.4 percent).

$^1$H NMR (400 MHz, D$_2$O); 2.05 (s, 3H), 2.60-2.70 (m, 2H), 5.1 (dd, 1H, J=7.5, 7.5 Hz), 6.88 (d, 2H, J=8.6 Hz), 7.26 (d, 2H, J=8.6 Hz)

ESI-MS [M-H]=222

2-8. Synthesis of N-acetyl-(R,S)-4-fluoro-β-Phe (R,S)-4-Fluoro-β-Phe (206 mg, 1.12 mmol) was suspended in 16 mL of water, 20 percent NaOH aqueous solution was added, and the pH was adjusted to a range of 11 to 12. While maintaining the pH of the aqueous solution within the range of 11 to 12 by adjusting the pH with 20 percent NaOH aqueous solution, acetic anhydride (0.22 mL, 2.26 mmol) was added drop-by-drop at room temperature. The reaction mixture was filtered to remove insoluble material, concentrated hydrochloric acid was added to the solution, the pH was adjusted to 2, and the solution was concentrated in an evaporator, causing crystals to precipitate out. The crystals were filtered out, washed with water, and dried overnight at 50° C. under reduced pressure, yielding N-acetyl-(R,S)-4-fluoro-β-Phe (143.9 mg, 0.64 mmol, 57.1 percent).

ESI-MS [M-H]=224

After obtaining the crystals, a chart was determined by NMR for the above compound, and mass spectroscopy was conducted to confirm that the targeted compound had indeed been produced.

2-9. Synthesis of N-acetyl-(R,S)-β-aminobutyric acid

Methyl 3-acetamide-2-butenoate was prepared by the method described in *J. Am. Chem. Soc.* 2002, 124, 14552.

To a methanol solution of methyl 3-acetamide-2-butenoate (1.35 g), 5 percent palladium/active carbon was added, and the mixture was stirred for 16 hours at 30° C. under 1 atmosphere of hydrogen. When the reaction had ended, the 5 percent palladium/active carbon was removed by filtration, and the solution obtained was concentrated, yielding methyl 3-acetamide-2-butyrate (1.37 g).

To a 3 mL ethanol solution of the methyl 3-acetamide-2-butenoate (570 mg), an 8 M hydroxide aqueous solution (900 μL) was added and the mixture was stirred for one hour at 35° C. When the reaction had ended, the reaction solution was neutralized by adding 6 M hydrochloric acid (1.2 mL), and concentrated. Dichloromethane (20 mL) was added. The precipitating crystals were removed by filtration and the filtrate was concentrated, yielding 265 mg of the title compound.

Production of the target compound was confirmed by NMR.

$^1$H NMR (400 MHz, MeOH-d4); 1.41 (q, 3H, J=2.6 Hz), 1.99 (s, 3H), 2.55 (t, 2H, J=5.1 Hz), 4.28 (m, 1H)

$^{13}$C NMR (400 MHz, MeOH-d4); 175.6, 170.88, 42.62, 40.22, 23.60, 20.34

ESI-MS [M-H]=144

2-10. N-Acetyl-3,4-(—O—CH2—O—)-β-phenylalanine

This compound was prepared by the method described in US20060035345.

2-11. Synthesis of N-acetyl-(R,S)-3-Pyr-Ala

β-3-Pyr-Ala (200 mg, 1.2 mmol) was suspended in 5 mL of water and 20 percent NaOH aqueous solution was added to adjust the pH to a range of 11 to 12. While maintaining the pH of the aqueous solution within the range of 11 to 12 by adjusting the pH with 20 percent NaOH aqueous solution, acetic anhydride (257 mL, 2.46 mmol) was added drop-by-drop at room temperature. The reaction mixture was filtered to remove insoluble material, concentrated hydrochloric acid was added to the solution, and the pH was adjusted to 2. Since nothing precipitated out, an evaporator was used to completely evaporate off the liquid. The dried product was analyzed by NMR and employed in the reaction.

$^1$H NMR (400 MHz, D2O); 2.03 (s, 3H), 2.78-2.90 (m, 2H), 5.33 (dd, 1H, J=7.3, 7.3 Hz), 7.97 (dd, 1H, J=5.7, 8.2 Hz), 8.49 (d, 1H, J=8.2 Hz), 8.67 (d, 1H, J=5.7 Hz), 8.75 (s, 1H)

ESI-MS [M-H]=207

3. Measurement of Enzymatic Activity 3-1. Assay Conditions 10 mM N acetyl-(R,S)-β-Phe, 50 mM Tris-HCl (pH 7.6), and a reaction solution containing a suitable enzyme sample were left standing from 15 minutes to 2 hours at 30° C., and then processed by boiling for 5 minutes to stop the reaction. The reaction solution was centrifuged. The supernatant was suitably diluted and then analyzed by HPLC. Acylase activity that produced 1 μmol of (R)-β-Phe or (S)-β-Phe per minute under these standard reaction conditions was defined as one unit. Activity producing (R)-β-Phe from N-acetyl-(R,S)-β-Phe will be referred to as N-acetyl-(R)-β-Phe acylase activity and activity producing (S)-β-Phe will be referred to as N-acetyl-(S)-β-Phe acylase activity hereinafter.

3-2. HPLC 3-2-1. (R),(S)-β-Phe Optical Resolution Conditions (R)-β-Phe, (S)-β-Phe, N-acetyl-(R)-β-Phe, and N-acetyl-(S)-β-Phe were quantitatively analyzed. The column employed was an Inertsil ODS3 (0.46 cm in diameter, 5 cm) made by GL Science and a Chiralpak WH (0.46 cm in diameter, 25 cm) made by Daisel Chemical Industries, arranged consecutively in that order. The mobile phase was 0.25 mM $CuSO_4$, 2 percent (v/v) acetonitrile. The flow rate was 1.5 mL/minute. The column temperature was 50° C. Detection was conducted with a UV detector at 210 nm. In this analysis, the above four compounds eluted out at different elution times. The elution sequence, in order of elution speed, was (S)-β-Phe, (R)-β-Phe, N-acetyl-(R)-β-Phe, and N-acetyl-(S)-β-Phe. The quantities were calculated from the peak area values relative to various standard products.

3-2-2. N-acetyl-β-Phe and β-Phe Separation Conditions

An Inertsil Ph-3 (0.46 cm in diameter, 25 cm) column made by GL Science was employed. The mobile phase was 10 percent acetonitrile (adjusted to pH 3.0 with phosphoric acid). The temperature was 40° C. The flow rate was 1.0 mL/min. Detection was conducted under UV conditions of 210 nm and peak area values were calculated based on comparison with various standard racemic products.

3-2-3. (R), (S)-β-Leu, (R), (S)-β-homoLeu, (R), (S)-β-homoPhe Separation Conditions An Astec Chirobiotec T (0.46 cm in diameter, 25 cm) column was employed. A 90 percent MeOH mobile phase was employed. The temperature was 40° C. and the flow rate was 0.4 mL/minute. Optical selectivity was determined based on comparison with various standard (R) and (S) standard products under UV detection conditions of 205 nm.

3-2-4. (R), (S)-β-Tyr, (R), (S)-β-4-fluoro-phe Resolution Conditions.

The column employed was comprised of an Inertsil ODS3 (0.46 cm in diameter, 5 cm) made by GL Science and a Chiralpak WH (0.46 cm in diameter, 25 cm) made by Daisel Chemical Industries, arranged consecutively in that order. The mobile phase was 1 mM $CuSO_4$, 10 percent MeOH. The temperature was 50° C. and the flow rate was 1.0 mL/minute. Detection was conducted with a UV detector at 210 nm and optical selectivity was determined by comparison with standard (R) and (S) products.

4. Purification of N-acetyl-(R)/(S)-β-amino acid acylase Derived from *Burkholderia* sp. AJ110349

4-1. Bacterial Strain, Culturing, and Purification

*Burkholderia* sp. AJ110349 was employed. Preserved bacterial strain was refreshed by being statically cultured for 48 hours at 30° C. on CM2G agar medium comprised of 5 g/L of D-glucose, 10 g/L of yeast extract, 10 g/L of peptone, 5 g/L of NaCl, and 20 g/L of agar (pH 7.0). The refreshed bacteria were inoculated onto 100 mL of enzyme producing medium comprised of 10 g/L D-glucose, 10 g/L $(NH_4)_2SO_4$, 10 g/L (R,S)-β-Phe, 2 g/L casamino acid, 1 g/L $KH_2PO_4$, 0.4 g/L $MgSO_4 \cdot 7H_2O$, 1 g/L NaCl, 19.5 g/L 2-(N-morpholino)ethanesulfonic acid (MES), 5 mg/L nicotinamide, 0.2 mg/L thiamin, 10 mg/L $FeSO_4 \cdot 7H_2O$, 10 mg/L $MnSO_4 \cdot 4$ to $5H_2O$, and culturing was conducted with shaking in a 500 mL Sakaguchi flask for 66 hours at 120 rpm at 30° C.

4-2. Preparation of Cell-Free Extract

The bacterial cells were collected by a 6,800 g, 10 minute centrifugation operation from about 2,000 mL of culture solution. Since precipitation of the bacterial cells was not adequately observed, about 1,600 mL of supernatant was removed, and the remainder was rendered uniform by pipeting. This concentrated culture solution, without being washed by buffer or the like, was ultrasonically processed for 20 min at 200 W to rupture the bacteria. The ruptured solution obtained was centrifuged for 30 min at 200,000 g, and about 200 mL of the centrifuged supernatant obtained was employed as cell-free extract.

4-3. Ammonium Sulfate Fractionation $(NH_4)_2SO_4$ was added to the cell-free extract to a final concentration of 40 percent saturation. The mixture was stirred on ice for one hour and centrifuged for 15 minutes at 9,200 g. The precipitate obtained was dissolved in a small quantity of 25 mM Tris-HCl (pH 7.6) and then dialyzed against 25 mM Tris-HCl (pH 7.6). Following dialysis, the solution was employed as a sample in chromatography, described further below.

4-4. Chromatography 4-4-1. Phenyl Sepharose 26/10 (Amersham Pharmacia)

The ammonium sulfate fractions obtained as set forth above were dialyzed against a buffer solution comprised of 25 mM Tris-HCl (pH 7.6) and 0.6 M $(NH_4)_2SO_4$ and then placed on phenyl sepharose 26/10 that had been equilibrated with the same buffer solution. Following nonadsorptive protein elution, the adsorptive protein was eluted by linearly varying the $(NH_4)_2SO_4$ concentration in the buffer solution from 0.6 M to 0 M. This operation resulted in the N-acetyl-(R)-β-Phe acylase activity being detected when the $(NH_4)_2SO_4$ concentration was about 0.2 M, and the N-acetyl-(S)-β-Phe acylase activity being detected when the $(NH_4)_2SO_4$ concentration was about 0.1 M. The fractions exhibiting activity were divided into N-acetyl-(R)-β-Phe acylase activity elution fractions and N-acetyl-(S)-β-Phe acylase activity elution fractions and recovered.

4-4-2. Q-Sepharose 16/10 (Amersham Pharmacia)

The phenyl-sepharose fraction obtained was concentrated, and dialyzed against 25 mM Tris-HCl (pH 7.6), and then placed on Q-Sepharose 16/10 that had been equilibrated with the same buffer solution. Following nonadsorptive protein elution, the adsorptive protein was eluted by linearly varying the NaCl concentration in the buffer solution from 0 M to 0.5 M. This operation resulted in N-acetyl-(R)-β-Phe acylase activity being detected when the NaCl concentration was about 0.22 M, and the N-acetyl-(S)-β-Phe acylase activity being detected when the NaCl concentration was about 0.3 M. The fractions exhibiting activity were recovered.

4-4-3. Superdex 200 16/60 (Amersham Pharmacia)

The Q-Sepharose fraction obtained was concentrated and placed on a Superdex 200 16/20 equilibrated with 25 mM Tris-HCl (pH 7.6). This operation resulted in the detection of N-acetyl-(R)-β-Phe acylase activity at an elution position estimated to correspond to a molecular weight of 206 kDa, and the detection of N-acetyl-(S)-β-Phe acylase activity at an elution position estimated to correspond to a molecular weight of 101 kDa. The fractions exhibiting activity were recovered.

4-4-4. Resource Phenyl (Amersham Pharmacia)

The Superdex fractions obtained were concentrated, dialyzed against a buffer solution comprised of 25 mM Tris-HCl (pH 7.6) and 0.6 M $(NH_4)_2SO_4$, and then placed on Resource phenyl equilibrated with the same buffer solution. Following nonadsorptive protein elution, the adsorptive protein was eluted by linearly varying the $(NH_4)_2SO_4$ concentration in the buffer solution from 0.6 M to 0 M. This operation resulted in N-acetyl-(R)-β-Phe acylase activity being detected when the $(NH_4)_2SO_4$ concentration was about 0.35 M, and N-acetyl-(S)-β-Phe acylase activity being detected when the $(NH_4)_2SO_4$ concentration was about 0.45 M. The fractions exhibiting activity were recovered.

4-4-5. Mono Q 5/5 (Amersham Pharmacia)

The Resource phenyl fractions obtained were concentrated, dialyzed against 25 mM Tris-HCl (pH 7.6), and placed on Mono Q 5/5 equilibrated with the same buffer solution. Following nonadsorptive protein elution, the adsorptive protein was eluted by linearly varying the NaCl concentration in the buffer solution from 0 M to 0.5 M. This operation resulted in the N-acetyl-(R)-β-Phe acylase activity being detected when the NaCl concentration was about 0.2 M, and the N-acetyl-(S)-β-Phe acylase activity being detected when the NaCl concentration was about 0.28 M. The fractions exhibiting activity were recovered, and adopted as N-acetyl-(R)-β-amino acid acylase and N-acetyl-(S)-β-amino acid acylase preparations.

The results of the above enzyme purification have been organized into Table 1 (N-acetyl-(R)-β-amino acid acylase) and Table 2 (N-acetyl-(S)-β-amino acid acylase). These purification operations yielded N-acetyl-(R)-β-amino acid acylase with a specific activity that had been purified 262-fold, and N-acetyl-(S)-β-amino acid acylase with a specific activity that had been purified 809-fold.

TABLE 1

| Step | Protein (mg) | Activity (U) | Yield (%) | Specific activity (U/mg) | Purification (x fold) |
|---|---|---|---|---|---|
| Crude extract | 1438 | 68 | 100 | 0.047 | 1.0 |
| (NH$_4$)$_2$SO$_4$ precipitation | 1074 | 66 | 97 | 0.061 | 1.3 |
| Phenyl Sepharose | 36 | 50 | 74 | 1.4 | 29 |
| Q-Sepharose | 10 | 49 | 72 | 5.1 | 107 |
| Superdex 200 | 4.3 | 31 | 46 | 7.2 | 152 |
| Resource Phenyl | 0.81 | 7.6 | 11 | 9.4 | 198 |
| Mono-Q | 0.29 | 3.6 | 5.3 | 12.4 | 262 |

TABLE 2

| Step | Protein (mg) | Activity (U) | Yield (%) | Specific activity (U/mg) | Purification (x fold) |
|---|---|---|---|---|---|
| Crude extract | 1438 | 23 | 100 | 0.016 | 1.0 |
| (NH$_4$)$_2$SO$_4$ precipitation | 1074 | 19 | 83 | 0.016 | 1.0 |
| Phenyl Sepharose | 47 | 11 | 48 | 0.23 | 14 |
| Q-Sepharose | 6.5 | 6.2 | 27 | 0.95 | 59 |
| Superdex 200 | 1.4 | 3.4 | 15 | 2.4 | 150 |
| Resource Phenyl | 0.039 | 0.21 | 0.90 | 5.4 | 333 |
| Mono-Q | 0.013 | 0.17 | 0.73 | 13.1 | 809 |

4-5. SDS-PAGE

The refined N-acetyl-(R)-β-amino acid acylase and N-acetyl-(S)-β-amino acid acylase obtained as set forth above were subjected to SDS-PAGE (FIG. 1). As a result, the N-acetyl-(R)-β-amino acid acylase was observed as a single band estimated to have a molecular weight of about 84 kDa (FIG. 1A), and the N-acetyl-(S)-β-amino acid acylase was observed as a single band estimated to have a molecular weight of about 41 kDa (FIG. 1B). In the above gel filtration chromatography, the molecular weights of the two enzymes in their unaltered forms were estimated at 206 kDa (N-acetyl-(R)-β-amino acid acylase) and 101 kDa (N-acetyl-(S)-β-amino acid acylase). When considered along with the molecular weights estimated by SDS-PAGE, both of the enzymes were thought to have homodimer or homotrimer structures.

4-6. Optical Specificity

Figure 2:
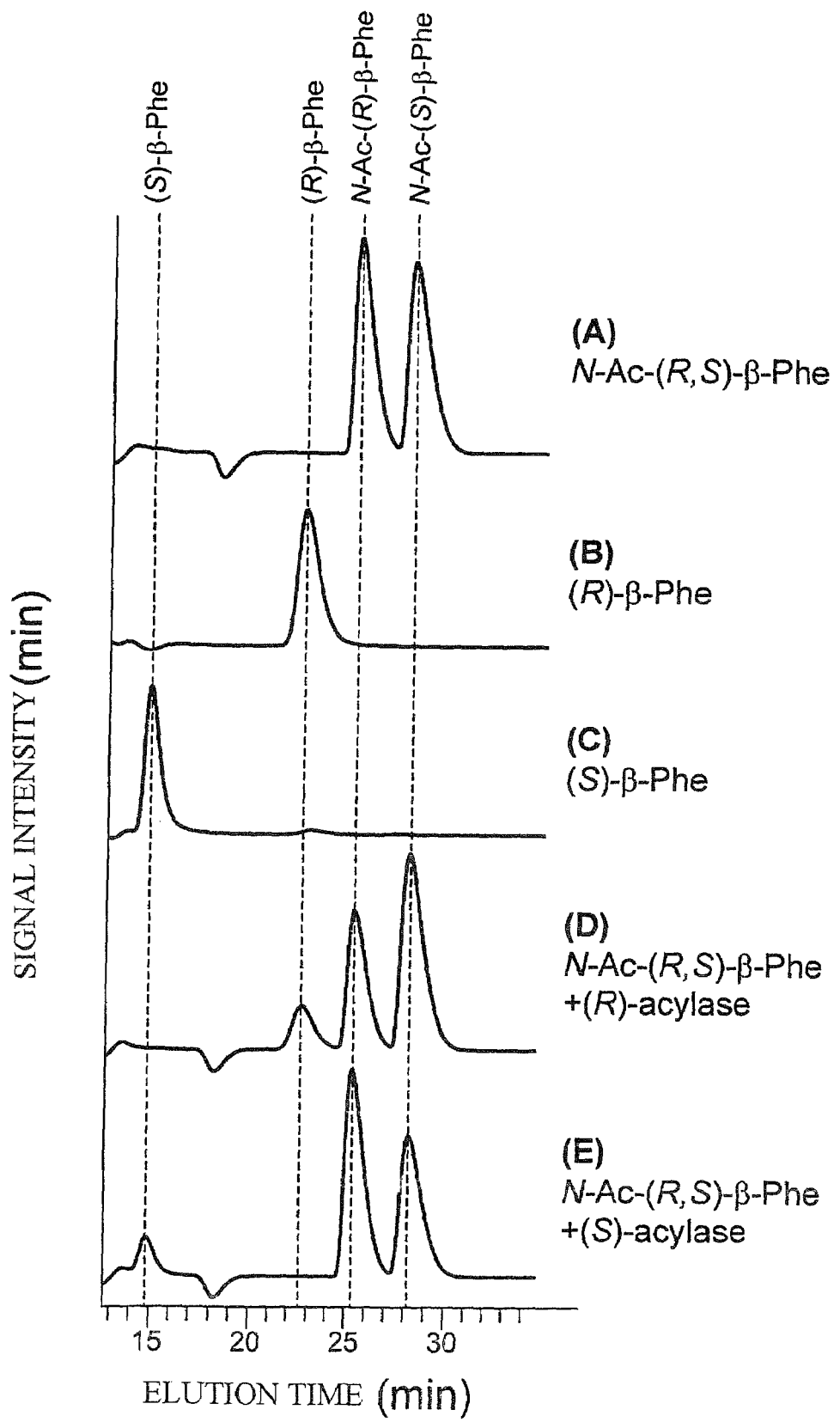
FIG. 2: The results of HPLC analysis of results obtained employing N-acetyl-(R,S)-β-Phe as substrate and making changes with purified N-acetyl-(R)-β-amino acid acylase or N-acetyl-(S)-β-amino acid acylase as enzyme source. (A) shows the results when no enzyme was added with only N-acetyl-(R,S)-β-Phe present; (B) shows the results when (R)-β-Phe was added; (C) shows the results when (S)-β-Phe was added; (D) shows the results when N-acetyl-(R,S)-β-Phe and N-acetyl-(R)-β-amino acid acylase were added; and (E) shows the results when N-acetyl-(R,S)-β-Phe and N-acetyl-(S)-β-amino acid acylase were added.

Optical selectivity was measured using the purified enzymes as enzyme sources. Reactions were conducted under the above enzyme conditions for a period of 30 minutes. The quantity of enzyme added was 4.6 μg/mL (N-acetyl-(R)-β-amino acid acylase) or 3.1 μg/mL (N-acetyl-(S)-β-amino acid acylase). As a result, only the production of (R)-β-Phe was observed when N-acetyl-(R)-β-amino acid acylase was employed as the enzyme source, with the production of (S)-β-Phe being below the detection threshold (FIG. 2D). Only the production of (S)-β-Phe was observed when N-acetyl-(S)-β-amino acid acylase was employed as the enzyme source, with the production of (R)-β-Phe being below the detection threshold (FIG. 2E). These results indicated that each of the enzymes had high optical selectively.

5. N-Terminal Amino Acid Sequence Analysis

The N-terminal amino acid sequences of the purified enzyme preparations were determined. This was done by subjecting the enzyme preparations to SDS-PAGE, transferring them to a PVDF membrane, staining them with coomassie blue, cutting out the positions where bands appeared, and placing these portions in a protein sequencer. As a result, N-acetyl-(R)-β-amino acid acylase was sequenced as the 20 residues indicated by SEQ. ID. NO. 1, and N-acetyl-(S)-β-amino acid acylase was sequenced as the 26 amino acid residues indicated by SEQ. ID. NO. 2.

6. Gene Cloning and Nucleotide Sequencing

Based on the N-terminal amino acid sequence that was determined, a synthetic primer was designed. An LAPCR in vitro Cloning Kit made by Takara Corp. was employed to obtain the partial gene fragment encoding acylase. As a result, a DNA fragment of 794 bases comprising a 5'-PstI recognition sequence and a 3'-EcoRI recognition sequence at its two ends, and containing the gene region encoding the N terminal of N-acetyl-(R)-β-amino acid acylase; and a DNA fragment of 393 bases having a 5'-PstI recognition sequence and a 3'-SalI recognition sequence at its two ends, and containing the gene region encoding the N terminal of N-acetyl-(S)-β-amino acid acylase, were obtained, and the nucleotide sequences were determined.

Based on the information obtained by determining the nucleotide sequences, primers R7F and R8R (SEQ. ID. NOS. 3 and 4) and primers S3F and S4R (SEQ. ID. NOS. 5 and 6) were employed to conduct PCR using genomic DNA of Burkholderia sp. AJ110349 as template. The 0.3 kg DNA fragment containing the gene region encoding the vicinity of the N-terminal of N-Acetyl-(R)-β-amino acid acylase, and the 0.4 kb DNA fragment containing the general region encoding the N-terminal of N-acetyl-(S)-β-amino acid acylase were amplified, DIG labeling was conducted, and these were denoted as R-probe and S-probe, respectively.

A 5 μg quantity of the chromosomal DNA of Burkholderia sp. AJ110349 was cleaved with BamHI and HindIII (100/50 U), after which R probe was used to conduct Southern analysis. The hybridization conditions were 42° C. and 16 hours; DIG Easy Hyb (Roche Corp.) was employed as the hybridization solvent. As a result, a positive signal was determined for roughly 5 kb.

A 5 μg quantity of the chromosomal DNA of Burkholderia sp. AJ110349 was cleaved with BamHI and HindIII (100/50 U), after which agarose electrophoresis was conducted. A fragment of about 5 kb was purified and ligated to the pUC118 BamrHI/HindIII sites. Escherichia coli JM109 was transformed with this reaction solution and a library was prepared. Using the above probe, colony hybridization was conducted. The positive colonies were collected and the plasmid was extracted. The plasmid obtained was designated as pBRACY_A3. When the nucleotide sequence of the insertion sequence was determined, an ORF (SEQ. ID. NO. 7) of 760 amino acids (SEQ. ID. NO. 8) was found to be present.

A 5 μg quantity of the chromosomal DNA of Burkholderia sp. AJ110349 was cleaved with PstI and HindIII (50 U each), and Southern analysis was conducted with the S-probe. The hybridization conditions were 42° C. and 16 hours. DIG Easy Hyb (Roche Corp.) was employed as the hybridization solution. As a result, a positive signal was determined for about 1.5 kb.

Next, agarose electrophoresis was conducted following processing of a 5 μg quantity of the chromosomal DNA of *Burkholderia* sp. AJ110349 with PstI and HindIII (50 U each). A fragment in the vicinity of 1.5 kb was purified and ligated to the PstI/HindIII sites of pUC118. *Escherichia coli* JM109 was transformed with this reaction solution and a library was prepared. Using the above probe, colony hybridization was conducted. The positive colonies were collected and the plasmid was extracted. The plasmid obtained was designated as pBSACY—PH. When the nucleotide sequence of the insertion sequence was determined, an ORF (SEQ. ID. NO. 9) of 352 amino acids (SEQ. ID. NO. 10) was found to be present.

7. Obtaining an N-acetyl-(R)-β-Amino Acid Acylase Gene Derived from *Variovorax* sp. AJ110348 by shotgun cloning Genomic DNA was extracted from *Variovorax* sp. AJ110348 and partially denatured with restrictase Sau3AI. Fragments of about 3 to 8 kb were recovered and ligated to pUC118. *Escherichia coli* JM109 was transformed with this reaction solution and a library was prepared.

The transformants obtained were sorted by blue white selection, and a master plate was prepared for the 3,500 strains obtained as single colonies. These bacterial strains were inoculated in groups of 10 strains each onto N-acetyl-(R,S)-β-Phe liquid medium (ammonium sulfate 10.0 g/L, $KH_2PO_4$ 1.0 g/L, $MgSO_4·7H_2O$ 0.4 g/L, $FeSO4·7H_2O$ 10 mg/L, $MnSO4·5H_2O$ 10 mg/L, vitamin B1·HCl 0.2 mg/L, N-acetyl-(R,S)-β-Phe 1.0 g/L, and pH 8.0 IPTG 100 μM Amp 100 μg/mL) and cultured with shaking for 48 hours at 37° C.

The supernatants of the cultures were separated with Siliagel $60F_{254}$ plates (Merck) and butanol: acetic acid:water 4:1:2, and the generation of β-Phe was confirmed by UV absorption at 254 nm and ninhydrin coloration.

As a result, since β-Phe was detected in the mixed culture supernatant, the same procedure was repeated for each strain. When the culture supernatants were determined by TLC, β-Phe was detected in a strain dubbed strain K83.

The plasmid DNA of strain K83 was extracted and the insertion sequence was determined, revealing the presence of an insertion sequence of about 3 kb. Nucleotide sequencing revealed the presence of an ORF (SEQ. ID. NO. 11) encoding 779 amino acids (SEQ. ID. NO. 12).

8. Measurement of the Activity and Optical Selectivity of Strain K83

The K83 strain obtained was precultured for 16 hours at 37° C. in LB medium containing 100 mg/L of ampicillin. A 1 mL quantity of the cultured bacterial cells was transferred to 50 mL of TB medium containing 100 mg/L of ampicillin and 1 mM of IPTG and cultured for 16 hours at 30° C. The bacterial cells obtained were centrifugally separated to concentrate the bacteria cells. This bacterial cells were washed with 50 mM Tris buffer solution (pH 7.6) and the same buffer solution was employed to prepare a bacterial cell suspension. Ultrasonic rupturing was employed to rupture the bacterial cells. A supernatant solution obtained by centrifugal separation (15,000 g, 10 minutes, 4° C.) was employed as a cell-free extract and reacted for 10 minutes at 37° C. with 50 mM Tris-HCl (pH 7.6) and 0.2 percent N-acetyl-β-Phe. When the N-acetyl-β-amino acid acylase activity was measured under the separation conditions of N-acetyl-β-Phe and β-Phe, a value of 2.3 U/mg was obtained.

When optical selectivity was determined by HPLC under β-Phe optical resolution conditions, (R)-β-Phe had been specifically produced, with (S)-β-Phe being below the detection threshold.

9. Preparation of a High-Expression Strain of N-acetyl-(R)-β-amino acid acylase Derived from *Burkholderia* sp. AJ110349

Employing chromosomal DNA of *Burkholderia* sp. AJ110349 as a template, PCR was conducted with primers R__7F (SEQ. ID. NO. 13) and R_R_HindIII (SEQ. ID. NO. 14). The 2.3 kb amplified fragment obtained was treated with BamHI and HindIII, inserted into the BamrHI/HindIII site of ptrp4 (Reference Document: Journal of Molecular Catalysis B: Enzymatic 32 (2005) 205-211) to create ptrp4__3BR. *Escherichia coli* JM109 was transformed with this plasmid. The transformant was called JM109/ptrp4__3BR.

JM109/ptrp4__3BR was cultured for 16 hours at 37° C. in LB medium containing 100 mg/L of ampicillin. 1 mL of the cultured bacterial cells was transplanted to 50 mL of M9 casamino acid medium containing 100 mg/L of ampicillin and cultured for 18 hours at 30° C. The bacterial cells obtained were centrifugally separated to concentrate the bacteria cells. The separated bacterial cells were washed with 50 mM Tris buffer solution (pH 7.6) and the same buffer solution was employed to prepare a bacterial cell suspension. Ultrasonic rupturing was employed to rupture the bacterial cells. A supernatant solution obtained by centrifugal separation (15,000 g, 10 minutes, 4° C.) was employed as a cell-free extract and reacted for 30 minutes at 37° C. with 50 mM Tris-HCl (pH 7.6) and 0.2 percent N-acetyl-(R,S)-β-Phe. The quantity of β-Phe produced was measured by HPLC. The N-acetyl-β-amino acid acylase activity was measured at 0.29 U/mg. Optical selectivity was determined by HPLC under β-Phe optical resolution conditions, revealing the specific production of (R)-β-Phe; (S)-β-Phe was below the detection threshold.

10. Preparation of a High-Expression Strain of N-Acetyl-(S)-β-amino acid acylase Derived from *Burkholderia* sp. AJ110349

Employing chromosomal DNA of *Burkholderia* sp. AJ110349 as template, PCR was conducted with primers S_F_NdeI__2 (SEQ. ID. NO. 15) and S_R_HindIII (SEQ. ID. NO. 16). The 1.1 kb amplified fragment obtained was treated with NdeI/BamHI. Separately, pSFN_Sm_Aet (Reference Document WO2006075486) was cleaved with NdeI/HindIII, and about 3 kb of DNA was excised and purified. DNA comprised of 1.1 kb of PCR product that had been treated with restriction nuclease was inserted at the NdeI/HindIII sites of this pSFN to obtain pSFN__2BS. *Escherichia coli* JM109 was transformed with this plasmid. The transformant was called JM109/pSFN__2BS.

The insert sequence of this plasmid starts from the 6th Met. The present invention inserts the sequence in the plasmid at the 1st Met. However, there is not much difference between these plasmids.

JM109/pSFN__2BS was precultured for 16 hours at 37° C. in LB medium containing 100 mg/L of ampicillin. 1 mL quantity of the cultured bacterial cells was transplanted to 50 mL of TB medium containing 100 mg/L of ampicillin and cultured for 16 hours at 30° C. The bacterial cells obtained was centrifugally separated to concentrate the bacteria cells. The bacterial cells were washed with 50 mM Tris buffer solution (pH 7.6) and the same buffer solution was employed to prepare a bacterial cell suspension. Ultrasonic rupturing was employed to rupture the bacterial cells. A supernatant solution obtained by centrifugal separation (15,000 g, 10 minutes, 4° C.) was employed as a cell-free extract. The N-acetyl-β-amino acid acylase activity, measured as above, was 0.33 U/mg. Optical selectivity determined by HPLC under β-Phe optical resolution conditions revealed the specific production of (S)-β-Phe; (R)-β-Phe was below the detection threshold.

11. Preparation of a High-Expression Strain of N-Acetyl-(R)-β-amino acid acylase Derived from *Variovorax* sp. AJ110348

Employing chromosomal DNA of *Variovorax* sp. AJ110348 as a template, PCR was conducted with primer VRACY_1F_NdeI (SEQ. ID. NO. 17) and VRACY_R_HindIII (SEQ. ID. NO. 18). The 2.4 kb amplified fraction obtained was treated with NdeI/HindIII. The DNA product was inserted at the NdeI/HindIII sites of the pSFN NdeI/HindIII purified product to obtain pSFN_1VR. *Escherichia coli* JM109 was transformed with this plasmid. The transformant was called JM109/pSFN_1VR.

JM109/pSFN_1VR was cultured for 16 hours at 37° C. in LB medium containing 100 mg/L of ampicillin. 1 mL quantity of the cultured bacterial cells was transplanted to 50 mL of TB medium containing 100 mg/L of ampicillin and cultured for 16 hours at 30° C. The bacterial cells obtained were centrifugally separated to concentrate the bacteria cells.

The separated bacterial cells were washed with 50 mM Tris buffer solution (pH 7.6) and the same buffer was used to prepare a bacterial cell suspension. Ultrasonic rupturing was employed to rupture the bacterial cells. A supernatant solution obtained by centrifugal separation (15,000 g, 10 minutes, 4° C.) was employed as a cell-free extract. The N-acetyl-β-amino acid acylase activity, measured as above, was 1.5 U/mg. Optical selectivity determined by HPLC under β-Phe optical resolution conditions revealed the specific production of (R)-β-Phe; (S)-β-Phe was below the detection threshold.

12. Examination of Substrate Specificity 12.1 Examination of Substrate Specificity for Various N-Acetyl-(R,S)-β-Amino Acids JM109/ptrp4_3BR, JM109/pSFN_2BS, and JM109/pSFN_1VR were precultured for 16 hours at 37° C. in LB medium containing 100 mg/L of ampicillin. 1 mL quantity of the cultured bacterial cells was transplanted to 50 mL of TB medium containing 100 mg/L of ampicillin and cultured for 16 hours at 30° C. The bacterial cells obtained were centrifugally separated to concentrate the bacteria cells. The bacterial cells were washed with 50 mM Tris buffer solution (pH 7.6) and the same buffer solution was used to prepare a bacterial cell suspension. Ultrasonic rupturing was employed to rupture the bacterial cells. A supernatant solution obtained by centrifugal separation (15,000 g, 10 minutes, 4° C.) was employed as a cell-free extract, and substrate specificity for the various N-acetyl-(R,S)-β-amino acids described above in Embodiments 2-1 to 9 was examined.

After adjusting the enzymes by the above methods, their activity was measured. Activity producing 1 μmol of β-Phe per minute from N-acetyl-(R,S)-β-Phe was denoted as 1 U. In the various examination of substrate specificity, 50 mU cell-free extracts were employed. As a negative control, instead of the cell-free medium prepared as set forth above, a 50 mM Tris buffer solution (pH 7.6) that had been reacted with each of the substrates was employed as an "Enzyme-" test zone, and instead of the individual substrates, 50 mM Tris buffer solution (pH 7.6) that had been reacted with each of the cell-free extracts was employed as a "Substrate-" test zone.

50 mM Tris-HCl (pH 7.6) and 0.2 percent of various N-acetyl-(R,S)-β-amino acids were reacted at 37° C. for 1 hour or 24 hours, and then processed for 10 minutes at 96° C. to stop the reactions. The quantity of acetic acid produced by the decomposition of acetyl groups was determined by the protocol of an acetic acid kit (Roche).

Table 3 shows the quantity of acetic acid produced after one hour, and Table 4 shows the quantity of acetic acid produced after 24 hours. As a result, acetic acid was detected from test zones employed N-acetyl-(R,S)-β-aminobutyric acid (N-acetyl-13-Aba), N-acetyl-(R,S)-β-Leu, N-acetyl-(R,S)-β-homoLeu, N-acetyl-(R,S)-β-Tyr, N-acetyl-(R,S)-homophe, and N-acetyl-(R,S)-β-4-fluoroPhe as test zones.

TABLE 3

| | Concentration of acetic acid detected (mM) | | | |
|---|---|---|---|---|
| | JM109/ ptrp4_3BR | JM109/ pSFN_2BS | JM109/ pSFN_1VR | enzyme- |
| N-Ac-β-Phe | 5.0 | 5.3 | 5.2 | 0.1 |
| N-Ac-β-Aba | 0.1 | 0.1 | 0.0 | 0.0 |
| N-Ac-β-Leu | 0.2 | 1.6 | 0.0 | 0.0 |
| N-Ac-β-homoLeu | 3.0 | 1.2 | 0.0 | 0.0 |
| N-Ac-β-homoPhe | 1.6 | 0.5 | 0.1 | 0.0 |
| N-Ac-β-Tyr | 4.5 | 5.2 | 5.1 | 0.0 |
| N-Ac-β-4-F-Phe | 4.6 | 5.2 | 4.6 | 0.0 |
| Substrate- | 0.0 | 0.0 | 0.0 | 0.0 |

TABLE 4

| | Concentration of acetic acid detected (mM) | | | |
|---|---|---|---|---|
| | JM109/ ptrp4_3BR | JM109/ pSFN_2BS | JM109/ pSFN_1VR | enzyme- |
| N-Ac-β-Aba | 0.6 | 0.3 | 0.1 | 0.0 |
| N-Ac-β-Leu | 5.6 | 6.2 | 1.0 | 0.0 |
| N-Ac-β-homoLeu | 7.5 | 5.4 | 0.6 | 0.0 |
| N-Ac-β-homoPhe | 3.7 | 4.0 | 2.6 | 0.0 |
| N-Ac-β-Tyr | 4.9 | 5.2 | 4.6 | 0.0 |
| N-Ac-β-4-F-Phe | 5.4 | 5.1 | 4.7 | 0.0 |
| Substrate- | 0.0 | 0.0 | 0.0 | 0.0 |

12-2. Determination of Optical Specificity

After reacting for 24 hours, the samples were analyzed with various chiral resolution columns to determine optical selectivity.

12-2-1. Separation of (R) and (S)-β-Leu

Under the resolution conditions of 3-2-3, standard samples were eluted in the order N-acetyl-(R,S)-β-Leu; (S)-β-Leu, and (R)-β-Leu.

In the N-acetyl-β-Leu reaction solution employing JM109/ptrp4_3BR, (R)-β-Leu was detected and (S)-β-Leu was below the detection threshold; >99% ee.

In the N-acetyl-β-Leu reaction solution employing JM109/pSFN-2BS, (S)-β-Leu was detected and (R)-β-Leu was below the detection threshold; >99% ee.

In the N-acetyl-β-Leu reaction solution employing JM109/pSFN_1VR, (R)-β-Leu was detected and (S)-β-Leu was below the detection threshold; >99% ee.

12-2-2. Separation of (R) and (S)-homoLeu

Under the resolution conditions of 3-2-3., standard samples were eluted in the order N-acetyl-(R,S)-β-homoLeu; (R)-β-homoLeu, and (S)-β-homoLeu.

In the N-acetyl-β-homoLeu reaction solution employing JM109/ptrp4_3BR, (S)-β-homoLeu was detected and a small quantity of (R)-β-Leu was detected; 69% ee.

In the N-acetyl-β-homoLeu reaction solution employing JM109/pSFN-2BS, (R)-β-homoLeu was detected and (S)-β-Leu was below the detection threshold; >99% ee.

In the N-acetyl-β-homoLeu reaction solution employing JM109/pSFN__1VR, (S)-β-homoLeu was detected and (R)-β-homoLeu was below the detection threshold; >99% ee.

12-2-3. Separation of (R) and (S)-β-homoPhe

Under the resolution conditions of 3-2-3., standard samples were eluted in the order N-acetyl-(R,S)-homoPhe; (R)-β-homoPhe, and (S)-β-homoPhe.

In the N-acetyl-β-homoPhe reaction solution employing JM109/ptrp4__3BR, (S)-β-homoPhe was detected and a trace amount of (R)-β-homoPhe was detected; 98% ee.

In the N-acetyl-β-homoPhe reaction solution employing JM109/pSFN-2BS, (R)-β-homoPhe was detected and (S)-β-[homoPhe] was below the detection threshold; >99% ee.

In the N-acetyl-β-homoPhe reaction solution employing JM109/pSFN__1VR, (S)-β-homoPhe was detected and (R)-β-homoPhe was below the detection threshold; >99% ee.

12-2-4. Separation of (R) and (S)-β-Tyr

Under the resolution conditions of 3-2-4, standard samples were eluted in the order (S)-β-Tyr; (R)-β-Tyr, N-acetyl-(R)/(S)-β-Tyr. (The standard product of N-acetyl-β-Tyr was racemic, so the order of elution during separation was undetermined.)

In the N-acetyl-β-Tyr reaction solution employing JM109/ptrp4__3BR, (R)-β-Tyr was detected and a small amount of (S)-β-Tyr was detected; 61% ee.

In the N-acetyl-β-Tyr reaction solution employing JM109/pSFN-2BS, (S)-β-Tyr was detected and (R)-β-Tyr was below the detection threshold; >99% ee.

In the N-acetyl-β-Tyr reaction solution employing JM109/pSFN__1VR, (R)-β-Tyr was detected and (S)-β-Tyr was below the detection threshold; >99% ee.

12-2-5. Separation of (R), (S)-4-fluoro-β-Phe

Under the resolution conditions of 3-2-4., standard samples were eluted in the order (S)-4-fluoro-β-Phe, (R)-4-fluoro-β-Phe, and N-acetyl-(R)/(S)-4-fluoro-β-Phe. (The standard product of N-acetyl-4-fluoro-β-Phe was racemic, so the order of elution during separation was undetermined.)

In the N-acetyl-4-fluoro-β-Phe reaction solution employing JM109/ptrp4__3BR, (R)-4-fluoro-β-Phe was detected and a small amount of (S)-4-fluoro-β-Phe was detected; 94% ee.

In the N-acetyl-4-fluoro-β-Phe reaction solution employing JM109/pSFN__2BS, (S)-4-fluoro-β-Phe was detected and (R)-4-fluoro-β-Phe was below the detection threshold >99% ee.

In the N-acetyl-4-fluoro-β-Phe reaction solution employing JM109/pSFN__1VR, (R)-4-fluoro-β-Phe was detected and (S)-4-fluoro-β-Phe was below the detection threshold; >99% ee.

12-3. Examination of Substrate Specificity for N-acetyl-3,4-(O—CH2—O—)-β-phenylalanine JM109/ptrp4__3BR, JM109/pSFN__2BS, and JM109/pSFN__1VR were prepared by the methods set forth above, and their substrate specificity for N-acetyl-3,4-(O—CH2—O—)-β-phenylalanine was examined.

A 300 μL quantity of culture solution was washed with 50 mM Tris-HCl (pH 7.6), suspended in 300 μL of 50 mM Tris-HCl (pH 7.6), and subjected to ultrasonic rupturing to rupture the bacteria. A supernatant solution obtained by centrifugal separation (15,000 g, 10 minutes, 4° C.) was employed as cell-free extract in the reaction.

50 mM Tris-HCl (pH 7.6) and 0.2 percent N-acetyl-(R,S)-3,4-(—O—CH2—O—)-β-phenylalanine were reacted for 10 minutes at 37° C. When 3,4-(—O—CH2—O—)-β-phenylalanine was quantized under the separation conditions of N-acetyl-β-Phe and β-Phe, the activity per mL of cell-free extract was 0.2 U for JM109/ptrp4__3BR, 3.9 U for JM109/pSFN__2BS, and 27.8 U for JM109/pSFN__1VR.

When the standard product was separated under (R), (S)-β-Phe optical resolution conditions, (S)-3,4-(—O—CH2—O—)-β-phenylalanine, (R)-3,4-(—O—CH2—O—)-β-phenylalanine, and N-acetyl-(R)/(S)-3,4-(—O—CH2—O—)-β-phenylalanine eluted out sequentially (the elution order of N-acetyl-(R)/(S)-3,4-(—O—CH2—O—)-β-phenylalanine was undetermined).

When the reaction solution was analyzed under these conditions, (R)-3,4-(—O—CH2—O—)-β-phenylalanine was detected in the reaction solution of JM109/ptrp4__3BR, (S)-3,4-(—O—CH2—O—)-β-phenylalanine was detected in the reaction solution of JM109/pSFN__2BS, and (R)-3,4-(—O—CH2—O—)-β-phenylalanine was detected in the reaction solution of JM109/pSFN__1VR.

12-4. Examination of Substrate Specificity for N-acetyl-3-Pyr-Ala

Various enzymes were prepared from the same bacterial cells and by the same methods as in 12-1, and 50 mU cell-free extracts were employed in the reaction. 50 mM Tris-HCl (pH 7.6) and 1 percent N-acetyl-(R,S)-β-3-Pyr-Ala were reacted for 1 hour at 37° C., after which the reaction was stopped by treatment at 70° C. for 10 minutes. The quantity of acetic acid generated by the decomposition of acetyl groups was determined by the protocol of an acetic acid kit (Roche).

As a result, acetic acid was detected in concentrations of 3.5 mM, 8.4 mM, and 0.8 mM in the reaction solutions in which JM109/ptrp4__3BR, JM109/pSFN__2BS, and JM109/pSFN__1VR were employed, respectively, and no acetic acid was detected in the "Substrate-" or "Enzyme-" test zones.

13. Evaluation of Accumulated Quantities

JM109/ptrp4__3BR, JM109/pSFN-2BS, and JM109/pSFN__1VR were precultured for 16 hours at 37° C. in LB medium containing 100 mg/L of ampicillin. Single mL quantities of the cultured bacterial cells were transplanted to 50 mL of TB medium containing 100 mg/L of ampicillin and cultured for 16 hours at 30° C. The bacterial cells obtained were centrifugally separated to concentrate the bacteria cells. The bacterial cells were then washed with 50 mM Tris buffer solution (pH 7.6) and concentrated 10-fold with the same buffer solution to prepare bacterial suspensions.

These bacterial suspensions were reacted with 100 mM Tris-HCl (pH 7.6) and 5 percent N-acetyl-(R,S)-β-Phe for 24 hours at 37° C. at a total quantity of 2.5 mL. Subsequently, the reaction solutions were analyzed by the analysis method of 3-2-1.

When 500 μL of the 10-fold concentrated bacterial suspension of JM109/ptrp4__3BR was added and reacted, the (R)-β-Phe yield was 21.6 percent, >99% ee., and (S)-β-Phe was below the detection threshold.

When 250 μL of the 10-fold concentrated bacterial suspension of JM109/pSFN-2BS was added and reacted, the (S)-β-Phe yield was 49.5 percent, >99% ee, and (R)-β-Phe was below the detection threshold.

When 125 μL of the 10-fold concentrated bacterial suspension of JM109/pSFN__1VR was added and reacted, the (R)-β-Phe yield was 45.5 percent, >99% ee, and (S)-β-Phe was below the detection threshold.

INDUSTRIAL APPLICABILITY

Transformation of a host such as *Escherichia coli* with the genes identified in the present invention permits the construction of high-expression systems for N-acetyl-(R)-β-amino acid acylase and N-acetyl-(S)-β-amino acid acylase. As a result, these enzymes can be used to conveniently and economically provide systems that select for R and S-forms of β-aminoacids.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

What is claimed is:

1. A method for manufacturing β-amino acids comprising:
   a) contacting a microorganism which has been transformed with a gene with an N-acetyl-β-amino acid,
   b) inducing the production of the β-amino acid, and
   c) recovering the β-amino acid;
   wherein said gene comprises a DNA selected from the group consisting of:
   (A) DNA comprising the nucleotide sequence shown in SEQ ID NO: 7;
   (B) DNA encoding a protein having N-acetyl-(R)-β-amino acid acylase activity, wherein said DNA is able to hybridize under stringent conditions with a DNA which is complementary to the nucleotide sequence shown in SEQ ID NO: 7; and
   (C) DNA encoding a protein having N-acetyl-(R)-β-amino acid acylase activity, wherein the DNA has 95% or greater sequence homology with the nucleotide sequence shown in SEQ ID NO: 7;
   and wherein said stringent conditions comprise washing at 60° C. with 1×SSC, and 0.1 percent SDS.

2. A method for manufacturing β-amino acids comprising:
   a) contacting a protein having N-acetyl-β-amino acid acylase activity obtained from the microorganism which has been transformed with a gene with an N-acetyl-β-amino acid,
   b) inducing the production of the β-amino acid, and
   c) recovering the β-amino acid;
   wherein said gene comprises a DNA selected from the group consisting of:
   (A) DNA comprising the nucleotide sequence shown in SEQ ID NO: 7;
   (B) DNA encoding a protein having N-acetyl-(R)-β-amino acid acylase activity, wherein said DNA is able to hybridize under stringent conditions with a DNA which is complementary to the nucleotide sequence shown in SEQ ID NO: 7; and
   (C) DNA encoding a protein having N-acetyl-(R)-β-amino acid acylase activity, wherein the DNA has 95% or greater sequence homology with the nucleotide sequence shown in SEQ ID NO: 7;
   and wherein said stringent conditions comprise washing at 60° C. with 1×SSC and 0.1 percent SDS.

3. A method for manufacturing β-amino acids comprising:
   a) contacting a microorganism which has been transformed with a gene with an N-acetyl-β-amino acid,
   b) inducing the production of the β-amino acid, and
   c) recovering the β-amino acid;
   wherein said gene comprises a DNA selected from the group consisting of:
   (A) DNA comprising the nucleotide sequence shown in SEQ. ID. NO. 9;
   (B) DNA encoding a protein having N-acetyl-(S)-β-amino acid acylase activity, wherein said DNA is able to hybridize under stringent conditions with a DNA which is complementary to the nucleotide sequence shown in SEQ ID NO: 9; and
   (C) DNA encoding a protein having N-acetyl-(S)-β-amino acid acylase activity, wherein the DNA has 95% or greater sequence homology with the nucleotide sequence shown in SEQ ID NO: 9;
   and wherein said stringent conditions comprise washing at 60° C. with 1×SSC and 0.1 percent SDS.

4. A method for manufacturing β-amino acids comprising:
   a) contacting a protein having N-acetyl-β-amino acid acylase activity obtained from a microorganism transformed with a gene with an N-acetyl-β-amino acid,
   b) inducing the production of the β-amino acid, and
   c) recovering the β-amino acid;
   wherein said gene comprises a DNA selected from the group consisting of:
   (A) DNA comprising the nucleotide sequence shown in SEQ. ID. NO. 9;
   (B) DNA encoding a protein having N-acetyl-(S)-β-amino acid acylase activity, wherein said DNA is able to hybridize under stringent conditions with a DNA which is complementary to the nucleotide sequence shown in SEQ ID NO: 9; and
   (C) DNA encoding a protein having N-acetyl-(S)-β-amino acid acylase activity, wherein the DNA has 95% or greater sequence homology with the nucleotide sequence shown in SEQ ID NO: 9;
   and wherein said stringent conditions comprise washing at 60° C. with 1×SSC and 0.1 percent SDS.

* * * * *

SEQUENCE LISTING

```
<160> NUMBER OF SEQ ID NOS: 18

<210> SEQ ID NO 1
<211> LENGTH: 20
<212> TYPE: PRT
<213> ORGANISM: Burkholderia sp. AJ110349

<400> SEQUENCE: 1

Met Ile Thr Ile Thr Gly Tyr Ser Asp Val Leu Ser Ala Gly Pro Gly
1               5                   10                  15

Glu Thr Val Glu
            20

<210> SEQ ID NO 2
<211> LENGTH: 26
<212> TYPE: PRT
<213> ORGANISM: Burkholderia sp. AJ110349

<400> SEQUENCE: 2

Asn Asp Leu Ala Ser Arg Lys Gly Arg Ile Gln Thr Val Leu Gly Leu
1               5                   10                  15

Ile Asp Pro His Glu Leu Gly Pro Ala Leu
            20                  25

<210> SEQ ID NO 3
<211> LENGTH: 31
<212> TYPE: DNA
<213> ORGANISM: Artificial Sequence
<220> FEATURE:
<223> OTHER INFORMATION: R7F Primer

<400> SEQUENCE: 3
cgaggatccg cagcaggttc aggtcgatat c                                  31

<210> SEQ ID NO 4
<211> LENGTH: 33
<212> TYPE: DNA
<213> ORGANISM: Artificial Sequence
<220> FEATURE:
<223> OTHER INFORMATION: R8R Primer

<400> SEQUENCE: 4
gaattcgacg gtttcgccgg gtccggctga aag                                33

<210> SEQ ID NO 5
<211> LENGTH: 30
<212> TYPE: DNA
<213> ORGANISM: Artificial Sequence
<220> FEATURE:
<223> OTHER INFORMATION: S3F Primer

<400> SEQUENCE: 5
ctgcagccac acaccgggag gagaagtgcc                                    30

<210> SEQ ID NO 6
<211> LENGTH: 30
<212> TYPE: DNA
<213> ORGANISM: Artificial Sequence
<220> FEATURE:
```

-continued

<223> OTHER INFORMATION: S4R Primer

<400> SEQUENCE: 6
ccgcgcgcat tccagcaac tcttcgacgg         30

<210> SEQ ID NO 7
<211> LENGTH: 2283
<212> TYPE: DNA
<213> ORGANISM: Burkholderia sp. AJ110349
<220> FEATURE:
<221> NAME/KEY: CDS
<222> LOCATION: (1)..(2283)

<400> SEQUENCE: 7

```
atg atc acg atc acc gga tac agc gac gtt ctt tca gcc gga ccc ggc     48
Met Ile Thr Ile Thr Gly Tyr Ser Asp Val Leu Ser Ala Gly Pro Gly
1               5                   10                  15 gaa acc gtc gaa ttc aag gtc tcc agc aag tcg ccg cac ccg ttc acc     96
Glu Thr Val Glu Phe Lys Val Ser Ser Lys Ser Pro His Pro Phe Thr
            20                  25                  30 gcc gaa ctg gtg cgc gtg att cac gcc gat ccc aat ccc gct ggc ccc    144
Ala Glu Leu Val Arg Val Ile His Ala Asp Pro Asn Pro Ala Gly Pro
        35                  40                  45 ggc atg cgc ttc gaa ccg ctc ggc cag gtg ttt tca ggt acg ttc gcg    192
Gly Met Arg Phe Glu Pro Leu Gly Gln Val Phe Ser Gly Thr Phe Ala
    50                  55                  60 tcg ttc gac aag ccg tta cta ccc ggt tct ttc gcc cgc gtg agc ggc    240
Ser Phe Asp Lys Pro Leu Leu Pro Gly Ser Phe Ala Arg Val Ser Gly
65                  70                  75                  80 gtg ccg gca gcg ggc tcc gcg gcc ggg ctc gtg gcc ggc gcc cgc atc    288
Val Pro Ala Ala Gly Ser Ala Ala Gly Leu Val Ala Gly Ala Arg Ile
                85                  90                  95 cgg cca act gcg ctc gcc cgc ggc gac cag tgc gtg atg tcg caa tgg    336
Arg Pro Thr Ala Leu Ala Arg Gly Asp Gln Cys Val Met Ser Gln Trp
            100                 105                 110 aac acg gca cgg cac gcg ggc ttc gcg ctg ctg gtg agc gag cga ggc    384
Asn Thr Ala Arg His Ala Gly Phe Ala Leu Leu Val Ser Glu Arg Gly
        115                 120                 125 ctc gaa ctg agg ctc ggc gcg ggc acg ggc gaa ccg cct gtg tgc gtg    432
Leu Glu Leu Arg Leu Gly Ala Gly Thr Gly Glu Pro Pro Val Cys Val
    130                 135                 140 cta tgc gcg gca cga ctc gag gtc cga tgg tac gac gtc tgg ttc gcg    480
Leu Cys Ala Ala Arg Leu Glu Val Arg Trp Tyr Asp Val Trp Phe Ala
145                 150                 155                 160 atc gac acc gca tcg aac cgg atc gag gtg ggc gtc acc gaa gtc gac    528
Ile Asp Thr Ala Ser Asn Arg Ile Glu Val Gly Val Thr Glu Val Asp
                165                 170                 175 ggc agt gtc gct gcg cca gtg cgg cac cga acg ctg caa atg ctc gac    576
Gly Ser Val Ala Ala Pro Val Arg His Arg Thr Leu Gln Met Leu Asp
            180                 185                 190 gct cga tgg cgc gcg ccg cac tcc gat gac gcc gcg gat ctg ctg atc    624
Ala Arg Trp Arg Ala Pro His Ser Asp Asp Ala Ala Asp Leu Leu Ile
        195                 200                 205 ggc gca ctc gaa gac ggt gcc ggc cgc cga gcg cat ttc aac ggc cag    672
Gly Ala Leu Glu Asp Gly Ala Gly Arg Arg Ala His Phe Asn Gly Gln
    210                 215                 220 atc gaa gcg cca ttt gtc gcc gac gcg ctg ccg tcg ccc gcc acg cct    720
Ile Glu Ala Pro Phe Val Ala Asp Ala Leu Pro Ser Pro Ala Thr Pro
225                 230                 235                 240 gca gct aca gtc gaa tac gcc gcg ccg cgc gca agc gac ttc agc aca    768
Ala Ala Thr Val Glu Tyr Ala Ala Pro Arg Ala Ser Asp Phe Ser Thr
```

-continued

```
                        245                 250                 255
gat gcg ctt tac gcc gcg tgg gat ttc gca cgt ggc atc gac acg ctg        816
Asp Ala Leu Tyr Ala Ala Trp Asp Phe Ala Arg Gly Ile Asp Thr Leu
            260                 265                 270 aag att gcc gat acg acg ccg cat gca cgc cat ggc acg ctg cag aac        864
Lys Ile Ala Asp Thr Thr Pro His Ala Arg His Gly Thr Leu Gln Asn
                275                 280                 285 ctg ccg acg cgc gcg gtg cgc agc agc gcg tgg aac ggg cgt gag cgc        912
Leu Pro Thr Arg Ala Val Arg Ser Ser Ala Trp Asn Gly Arg Glu Arg
            290                 295                 300 tgc tgg cgc acg gcg ccg gcc cac tat gcc gcc att cat ttc cac gac        960
Cys Trp Arg Thr Ala Pro Ala His Tyr Ala Ala Ile His Phe His Asp
305                 310                 315                 320 gac gat ctg cat gac gcc ggc tgg tcg acc gat ttt gcg ttc acc gtg       1008
Asp Asp Leu His Asp Ala Gly Trp Ser Thr Asp Phe Ala Phe Thr Val
                325                 330                 335 ccc gcg acg ctg aaa agc ggt gcc tac gca atg cgg ctg agc gtc gac       1056
Pro Ala Thr Leu Lys Ser Gly Ala Tyr Ala Met Arg Leu Ser Val Asp
            340                 345                 350 ggc gcc acc gac tac ctg ccc ttc tac gtt cgc ccc gaa ctg ggc cgc       1104
Gly Ala Thr Asp Tyr Leu Pro Phe Tyr Val Arg Pro Glu Leu Gly Arg
        355                 360                 365 ccg ggc gcc ccg ctc gta ttc gtc gcg gcg acc tac acg tat cag gcg       1152
Pro Gly Ala Pro Leu Val Phe Val Ala Ala Thr Tyr Thr Tyr Gln Ala
    370                 375                 380 tac gcg aac tac gcg cgc ggc aac ttc gac gcg gca ttg cgc gac aag       1200
Tyr Ala Asn Tyr Ala Arg Gly Asn Phe Asp Ala Ala Leu Arg Asp Lys
385                 390                 395                 400 gtc ggg cga tgg ggc gcc tat cca cac aat ccc gac gac cat ccg gaa       1248
Val Gly Arg Trp Gly Ala Tyr Pro His Asn Pro Asp Asp His Pro Glu
                405                 410                 415 gtc ggc ctc gcg acc tac aac ctg cat tcg gac ggc agc ggc gtg atg       1296
Val Gly Leu Ala Thr Tyr Asn Leu His Ser Asp Gly Ser Gly Val Met
            420                 425                 430 ttc tcg tca cgc ctg cgt ccg atg ctg acg atg cgt ccg ggc ttc ctc       1344
Phe Ser Ser Arg Leu Arg Pro Met Leu Thr Met Arg Pro Gly Phe Leu
        435                 440                 445 acc ttc gac gat tcg cgc ggc tcc ggt tgc cgc cat tac atc gcg gac       1392
Thr Phe Asp Asp Ser Arg Gly Ser Gly Cys Arg His Tyr Ile Ala Asp
    450                 455                 460 tcg cac ctg ctc gac tgg ctc gag cac gaa ggc ttt tcg ttc gac gtg       1440
Ser His Leu Leu Asp Trp Leu Glu His Glu Gly Phe Ser Phe Asp Val
465                 470                 475                 480 gtc acg gac gac gat ctg gag cgc ttc ggc gcc gcg ctg ctc gaa ccc       1488
Val Thr Asp Asp Asp Leu Glu Arg Phe Gly Ala Ala Leu Leu Glu Pro
                485                 490                 495 tat gcc gcg gtg ctc acg ggc acg cat ccc gag tac cac acg gcc gcg       1536
Tyr Ala Ala Val Leu Thr Gly Thr His Pro Glu Tyr His Thr Ala Ala
            500                 505                 510 acg ctc gac gcg cta gcc ggc tac aag cgc agc ggc ggc aac ctg gcc       1584
Thr Leu Asp Ala Leu Ala Gly Tyr Lys Arg Ser Gly Gly Asn Leu Ala
        515                 520                 525 tat ctg ggc ggc aac ggt ttc tac tgg cgc gtc ggc cgc tct gag cgt       1632
Tyr Leu Gly Gly Asn Gly Phe Tyr Trp Arg Val Gly Arg Ser Glu Arg
    530                 535                 540 gtg ccg ggc gcg ctt gag gtg cgg cgc acc gaa ggc ggc gtg cgc gcg       1680
Val Pro Gly Ala Leu Glu Val Arg Arg Thr Glu Gly Gly Val Arg Ala
545                 550                 555                 560 tgg gcg gct gaa gcg ggc gaa tac ttt cac gcg ctc gac ggc gaa tac       1728
```

```
                Trp Ala Ala Glu Ala Gly Glu Tyr Phe His Ala Leu Asp Gly Glu Tyr
                            565                 570                 575 ggc gga tta tgg cgc agc agc gcg cga acg ccg cag caa ctg gtt ggc      1776
Gly Gly Leu Trp Arg Ser Ser Ala Arg Thr Pro Gln Gln Leu Val Gly
            580                 585                 590 gtc ggt ttc agc tcg cag gga ccg ttc gaa gga tcg cat tac cgc gtg      1824
Val Gly Phe Ser Ser Gln Gly Pro Phe Glu Gly Ser His Tyr Arg Val
            595                 600                 605 ctc gac gcc gcg cgc agc cag ccc ggc ggc tcg ctg ctc aaa gac atc      1872
Leu Asp Ala Ala Arg Ser Gln Pro Gly Gly Ser Leu Leu Lys Asp Ile
            610                 615                 620 gcg ggg ccg ctg ttc ggc ggc tat ggc ctg tcc ggc ggc ggc gcg gcc      1920
Ala Gly Pro Leu Phe Gly Gly Tyr Gly Leu Ser Gly Gly Gly Ala Ala
625                 630                 635                 640 ggc ttc gaa ctg gat tcg acc gaa gct gcc gac ggc acg ccg gca aac      1968
Gly Phe Glu Leu Asp Ser Thr Glu Ala Ala Asp Gly Thr Pro Ala Asn
                645                 650                 655 gtc atc atc ctc gcc cgc tcc gaa agc cat agt gcc gcc ttt gga ccg      2016
Val Ile Ile Leu Ala Arg Ser Glu Ser His Ser Ala Ala Phe Gly Pro
            660                 665                 670 gcg ctc gac gcc ctg ctc tcg cac acg gca acg cgt gcg cgg aaa acg      2064
Ala Leu Asp Ala Leu Leu Ser His Thr Ala Thr Arg Ala Arg Lys Thr
            675                 680                 685 ccc gac acg ctg att cga tcc gag atc gtc tat tac gaa acc ggc tat      2112
Pro Asp Thr Leu Ile Arg Ser Glu Ile Val Tyr Tyr Glu Thr Gly Tyr
690                 695                 700 gga ggc gcg gtg ttc tcg gtc ggt tcg atc acg ttc tgc ggc gcg ctt      2160
Gly Gly Ala Val Phe Ser Val Gly Ser Ile Thr Phe Cys Gly Ala Leu
705                 710                 715                 720 tcg cac aac gac tat cgc aac gac gtg agt acg ctg ctg cga aac gtg      2208
Ser His Asn Asp Tyr Arg Asn Asp Val Ser Thr Leu Leu Arg Asn Val
                725                 730                 735 ctt atc cgc ttt tca cgc gac cgc ggt gca cag gct cac gcc gtg cct      2256
Leu Ile Arg Phe Ser Arg Asp Arg Gly Ala Gln Ala His Ala Val Pro
            740                 745                 750 gcc gtc gct cac acc gag gtc gac tga                                  2283
Ala Val Ala His Thr Glu Val Asp
            755                 760

<210> SEQ ID NO 8
<211> LENGTH: 760
<212> TYPE: PRT
<213> ORGANISM: Burkholderia sp. AJ110349

<400> SEQUENCE: 8

Met Ile Thr Ile Thr Gly Tyr Ser Asp Val Leu Ser Ala Gly Pro Gly
1               5                   10                  15

Glu Thr Val Glu Phe Lys Val Ser Ser Lys Ser Pro His Pro Phe Thr
                20                  25                  30

Ala Glu Leu Val Arg Val Ile His Ala Asp Pro Asn Pro Ala Gly Pro
            35                  40                  45

Gly Met Arg Phe Glu Pro Leu Gly Gln Val Phe Ser Gly Thr Phe Ala
        50                  55                  60

Ser Phe Asp Lys Pro Leu Leu Pro Gly Ser Phe Ala Arg Val Ser Gly
65                  70                  75                  80

Val Pro Ala Ala Gly Ser Ala Ala Gly Leu Val Ala Gly Ala Arg Ile
                85                  90                  95

Arg Pro Thr Ala Leu Ala Arg Gly Asp Gln Cys Val Met Ser Gln Trp
            100                 105                 110
```

```
Asn Thr Ala Arg His Ala Gly Phe Ala Leu Leu Val Ser Glu Arg Gly
        115                 120                 125

Leu Glu Leu Arg Leu Gly Ala Gly Thr Gly Glu Pro Pro Val Cys Val
130                 135                 140

Leu Cys Ala Ala Arg Leu Glu Val Arg Trp Tyr Asp Val Trp Phe Ala
145                 150                 155                 160

Ile Asp Thr Ala Ser Asn Arg Ile Glu Val Gly Val Thr Glu Val Asp
                165                 170                 175

Gly Ser Val Ala Ala Pro Val Arg His Arg Thr Leu Gln Met Leu Asp
            180                 185                 190

Ala Arg Trp Arg Ala Pro His Ser Asp Asp Ala Ala Asp Leu Leu Ile
        195                 200                 205

Gly Ala Leu Glu Asp Gly Ala Gly Arg Arg Ala His Phe Asn Gly Gln
    210                 215                 220

Ile Glu Ala Pro Phe Val Ala Asp Ala Leu Pro Ser Pro Ala Thr Pro
225                 230                 235                 240

Ala Ala Thr Val Glu Tyr Ala Ala Pro Arg Ala Ser Asp Phe Ser Thr
                245                 250                 255

Asp Ala Leu Tyr Ala Ala Trp Asp Phe Ala Arg Gly Ile Asp Thr Leu
            260                 265                 270

Lys Ile Ala Asp Thr Thr Pro His Ala Arg His Gly Thr Leu Gln Asn
        275                 280                 285

Leu Pro Thr Arg Ala Val Arg Ser Ser Ala Trp Asn Gly Arg Glu Arg
    290                 295                 300

Cys Trp Arg Thr Ala Pro Ala His Tyr Ala Ala Ile His Phe His Asp
305                 310                 315                 320

Asp Asp Leu His Asp Ala Gly Trp Ser Thr Asp Phe Ala Phe Thr Val
                325                 330                 335

Pro Ala Thr Leu Lys Ser Gly Ala Tyr Ala Met Arg Leu Ser Val Asp
            340                 345                 350

Gly Ala Thr Asp Tyr Leu Pro Phe Tyr Val Arg Pro Glu Leu Gly Arg
        355                 360                 365

Pro Gly Ala Pro Leu Val Phe Val Ala Ala Thr Tyr Thr Tyr Gln Ala
    370                 375                 380

Tyr Ala Asn Tyr Ala Arg Gly Asn Phe Asp Ala Ala Leu Arg Asp Lys
385                 390                 395                 400

Val Gly Arg Trp Gly Ala Tyr Pro His Asn Pro Asp Asp His Pro Glu
                405                 410                 415

Val Gly Leu Ala Thr Tyr Asn Leu His Ser Asp Gly Ser Gly Val Met
            420                 425                 430

Phe Ser Ser Arg Leu Arg Pro Met Leu Thr Met Arg Pro Gly Phe Leu
        435                 440                 445

Thr Phe Asp Asp Ser Arg Gly Ser Gly Cys Arg His Tyr Ile Ala Asp
    450                 455                 460

Ser His Leu Leu Asp Trp Leu Glu His Glu Gly Phe Ser Phe Asp Val
465                 470                 475                 480

Val Thr Asp Asp Asp Leu Glu Arg Phe Gly Ala Ala Leu Leu Glu Pro
                485                 490                 495

Tyr Ala Ala Val Leu Thr Gly Thr His Pro Glu Tyr His Thr Ala Ala
            500                 505                 510

Thr Leu Asp Ala Leu Ala Gly Tyr Lys Arg Ser Gly Gly Asn Leu Ala
        515                 520                 525
```

```
Tyr Leu Gly Gly Asn Gly Phe Tyr Trp Arg Val Gly Arg Ser Glu Arg
            530                 535                 540

Val Pro Gly Ala Leu Glu Val Arg Arg Thr Glu Gly Gly Val Arg Ala
545                 550                 555                 560

Trp Ala Glu Ala Gly Glu Tyr Phe His Ala Leu Asp Gly Glu Tyr
                565                 570                 575

Gly Gly Leu Trp Arg Ser Ser Ala Arg Thr Pro Gln Gln Leu Val Gly
            580                 585                 590

Val Gly Phe Ser Ser Gln Gly Pro Phe Glu Gly Ser His Tyr Arg Val
            595                 600                 605

Leu Asp Ala Ala Arg Ser Gln Pro Gly Gly Ser Leu Leu Lys Asp Ile
    610                 615                 620

Ala Gly Pro Leu Phe Gly Gly Tyr Gly Leu Ser Gly Gly Ala Ala
625                 630                 635                 640

Gly Phe Glu Leu Asp Ser Thr Glu Ala Ala Asp Gly Thr Pro Ala Asn
                645                 650                 655

Val Ile Ile Leu Ala Arg Ser Glu Ser His Ser Ala Ala Phe Gly Pro
                660                 665                 670

Ala Leu Asp Ala Leu Leu Ser His Thr Ala Thr Arg Ala Arg Lys Thr
            675                 680                 685

Pro Asp Thr Leu Ile Arg Ser Glu Ile Val Tyr Tyr Glu Thr Gly Tyr
    690                 695                 700

Gly Gly Ala Val Phe Ser Val Gly Ser Ile Thr Phe Cys Gly Ala Leu
705                 710                 715                 720

Ser His Asn Asp Tyr Arg Asn Asp Val Ser Thr Leu Leu Arg Asn Val
                725                 730                 735

Leu Ile Arg Phe Ser Arg Asp Arg Gly Ala Gln Ala His Ala Val Pro
            740                 745                 750

Ala Val Ala His Thr Glu Val Asp
        755                 760

<210> SEQ ID NO 9
<211> LENGTH: 1059
<212> TYPE: DNA
<213> ORGANISM: Burkholderia sp.AJ110349
<220> FEATURE:
<221> NAME/KEY: CDS
<222> LOCATION: (1)..(1059)

<400> SEQUENCE: 9 atg gat ttc tgc cag atg aac gat ctc gcc tca cga aag ggc cgc atc    48
Met Asp Phe Cys Gln Met Asn Asp Leu Ala Ser Arg Lys Gly Arg Ile
1               5                   10                  15 cag aca gtg ctt ggc ctg att gac ccg cac gag ctt ggg ccg gca ttg    96
Gln Thr Val Leu Gly Leu Ile Asp Pro His Glu Leu Gly Pro Ala Leu
            20                  25                  30 atg cac gag cat ctg ctg atc gat ctc gtg ccg cca aaa ctg gcc gaa    144
Met His Glu His Leu Leu Ile Asp Leu Val Pro Pro Lys Leu Ala Glu
        35                  40                  45 gac gcc gac cac gac cag acc gag atc gac ctg tgc aat tgc tgg aag    192
Asp Ala Asp His Asp Gln Thr Glu Ile Asp Leu Cys Asn Cys Trp Lys
    50                  55                  60 atc aac tat ggt cag gtg ccg tcg ctg aag aac tac cgg ctc gac cag    240
Ile Asn Tyr Gly Gln Val Pro Ser Leu Lys Asn Tyr Arg Leu Asp Gln
65                  70                  75                  80 aag gac gtg gcc gtc gaa gag ttg ctg gaa atg cgc gcg gcg ggc ggc    288
Lys Asp Val Ala Val Glu Glu Leu Leu Glu Met Arg Ala Ala Gly Gly
                85                  90                  95
```

-continued

| | | |
|---|---|---|
| agc gcg att gtc gac ttg acg acc ggc ggc ctg aaa ccc gat cca caa<br>Ser Ala Ile Val Asp Leu Thr Thr Gly Gly Leu Lys Pro Asp Pro Gln<br>        100                       105                 110 | | 336 |
| ggc ctc gcg cag att tca cgc gaa gcc ggc gtg cac gtc gtg atg ggg<br>Gly Leu Ala Gln Ile Ser Arg Glu Ala Gly Val His Val Val Met Gly<br>               115                     120                     125 | | 384 |
| tgt ggc cac tat gtg cat gag tat cag gac gcg gcc aat gcg cac cgg<br>Cys Gly His Tyr Val His Glu Tyr Gln Asp Ala Ala Asn Ala His Arg<br>130                       135                     140 | | 432 |
| tcg gtc gac gat ttc gcg agc gag atg atc ggc cag atc act gaa ggc<br>Ser Val Asp Asp Phe Ala Ser Glu Met Ile Gly Gln Ile Thr Glu Gly<br>145                 150                   155               160 | | 480 |
| gcg tgg ggc acg cag gtg cgc gcg ggc atc atc ggg gag ata ggc tgc<br>Ala Trp Gly Thr Gln Val Arg Ala Gly Ile Ile Gly Glu Ile Gly Cys<br>                     165                     170               175 | | 528 |
| cag tcg ccg tgg acg gag cag gag aag cgg gtg gtg cgg ggc gcg ttg<br>Gln Ser Pro Trp Thr Glu Gln Glu Lys Arg Val Val Arg Gly Ala Leu<br>                180                     185                   190 | | 576 |
| atc gcc cag cag gaa acc ggc gcg gcg ctg aac att cat ccc ggc cgc<br>Ile Ala Gln Gln Glu Thr Gly Ala Ala Leu Asn Ile His Pro Gly Arg<br>               195                     200                   205 | | 624 |
| cat gcg gag cag ccg cag gaa gtg atc gat acg atc aaa agt ctt ggc<br>His Ala Glu Gln Pro Gln Glu Val Ile Asp Thr Ile Lys Ser Leu Gly<br>210                       215                     220 | | 672 |
| tac ccg gtc gaa cgc gtc att atc agc cac atc gac cgt acg att ttc<br>Tyr Pro Val Glu Arg Val Ile Ile Ser His Ile Asp Arg Thr Ile Phe<br>225                       230                     235               240 | | 720 |
| gac gac acg agg ctc ctg agg ctt gcc gat tca ggc tgc gta att gag<br>Asp Asp Thr Arg Leu Leu Arg Leu Ala Asp Ser Gly Cys Val Ile Glu<br>                     245                     250               255 | | 768 |
| ctc gac ctg ttt ggc tgg gaa caa agc gcg tat ccg atg tcg gat atc<br>Leu Asp Leu Phe Gly Trp Glu Gln Ser Ala Tyr Pro Met Ser Asp Ile<br>               260                     265                   270 | | 816 |
| gac atg ccc aac gac ggc gca cgg ctg cgc atg gtg cgc acg ctg ctc<br>Asp Met Pro Asn Asp Gly Ala Arg Leu Arg Met Val Arg Thr Leu Leu<br>275                       280                     285 | | 864 |
| gat cac ggt cac gcg gag cga gtg ctg atc agc cac gac att tgc acc<br>Asp His Gly His Ala Glu Arg Val Leu Ile Ser His Asp Ile Cys Thr<br>               290                     295                   300 | | 912 |
| cgc acg cgc ctt ggg cgt tat ggc ggg cac ggt tat cag cac att ttt<br>Arg Thr Arg Leu Gly Arg Tyr Gly Gly His Gly Tyr Gln His Ile Phe<br>305                       310                     315               320 | | 960 |
| gcg aat gtc gtg ccg cgc atg ctg cgg cgc gat ttt acg cag gac gag<br>Ala Asn Val Val Pro Arg Met Leu Arg Arg Asp Phe Thr Gln Asp Glu<br>                       325                     330               335 | | 1008 |
| atc gat acg ctc ctc acg cgc aat ccg cgc cgc ctt ctg act ttc gtc<br>Ile Asp Thr Leu Leu Thr Arg Asn Pro Arg Arg Leu Leu Thr Phe Val<br>                     340                     345               350 | | 1056 |
| tag | | 1059 |

<210> SEQ ID NO 10
<211> LENGTH: 352
<212> TYPE: PRT
<213> ORGANISM: Burkholderia sp.AJ110349

<400> SEQUENCE: 10

Met Asp Phe Cys Gln Met Asn Asp Leu Ala Ser Arg Lys Gly Arg Ile
1               5                   10                  15

Gln Thr Val Leu Gly Leu Ile Asp Pro His Glu Leu Gly Pro Ala Leu

-continued

```
                          20                      25                      30
        Met His Glu His Leu Leu Ile Asp Leu Val Pro Pro Lys Leu Ala Glu
                      35                      40                      45

Asp Ala Asp His Asp Gln Thr Glu Ile Asp Leu Cys Asn Cys Trp Lys
                  50                      55                      60

Ile Asn Tyr Gly Gln Val Pro Ser Leu Lys Asn Tyr Arg Leu Asp Gln
         65                      70                      75                  80

Lys Asp Val Ala Val Glu Glu Leu Leu Glu Met Arg Ala Ala Gly Gly
                              85                      90                      95

Ser Ala Ile Val Asp Leu Thr Thr Gly Gly Leu Lys Pro Asp Pro Gln
                         100                     105                     110

Gly Leu Ala Gln Ile Ser Arg Glu Ala Gly Val His Val Val Met Gly
                     115                     120                     125

Cys Gly His Tyr Val His Glu Tyr Gln Asp Ala Ala Asn Ala His Arg
                 130                     135                     140

Ser Val Asp Asp Phe Ala Ser Glu Met Ile Gly Gln Ile Thr Glu Gly
        145                     150                     155                 160

Ala Trp Gly Thr Gln Val Arg Ala Gly Ile Ile Gly Glu Ile Gly Cys
                             165                     170                     175

Gln Ser Pro Trp Thr Glu Gln Glu Lys Arg Val Val Arg Gly Ala Leu
                         180                     185                     190

Ile Ala Gln Gln Glu Thr Gly Ala Ala Leu Asn Ile His Pro Gly Arg
                     195                     200                     205

His Ala Glu Gln Pro Gln Glu Val Ile Asp Thr Ile Lys Ser Leu Gly
                 210                     215                     220

Tyr Pro Val Glu Arg Val Ile Ile Ser His Ile Asp Arg Thr Ile Phe
        225                     230                     235                 240

Asp Asp Thr Arg Leu Leu Arg Leu Ala Asp Ser Gly Cys Val Ile Glu
                             245                     250                     255

Leu Asp Leu Phe Gly Trp Glu Gln Ser Ala Tyr Pro Met Ser Asp Ile
                         260                     265                     270

Asp Met Pro Asn Asp Gly Ala Arg Leu Arg Met Val Arg Thr Leu Leu
                     275                     280                     285

Asp His Gly His Ala Glu Arg Val Leu Ile Ser His Asp Ile Cys Thr
                 290                     295                     300

Arg Thr Arg Leu Gly Arg Tyr Gly Gly His Gly Tyr Gln His Ile Phe
        305                     310                     315                 320

Ala Asn Val Val Pro Arg Met Leu Arg Arg Asp Phe Thr Gln Asp Glu
                             325                     330                     335

Ile Asp Thr Leu Leu Thr Arg Asn Pro Arg Arg Leu Leu Thr Phe Val
                         340                     345                     350

<210> SEQ ID NO 11
<211> LENGTH: 2340
<212> TYPE: DNA
<213> ORGANISM: Variovorax sp. AJ110348
<220> FEATURE:
<221> NAME/KEY: CDS
<222> LOCATION: (1)..(2340)

<400> SEQUENCE: 11 atg acg atg cag cag cag aag atc ctc ccc ccg cac cgc agc ctg cag      48
Met Thr Met Gln Gln Gln Lys Ile Leu Pro Pro His Arg Ser Leu Gln
 1               5                  10                  15 gtg ccc ggc gtg cac ggc tac acc gac cgc aag agc gtg gcc gcc ggc      96
Val Pro Gly Val His Gly Tyr Thr Asp Arg Lys Ser Val Ala Ala Gly
```

-continued

```
                   20                    25                      30
gag gtg gtg cgc ttc cac atc agc agc gac gtg ccc tac acg ctc tcc      144
Glu Val Val Arg Phe His Ile Ser Ser Asp Val Pro Tyr Thr Leu Ser
         35                  40                      45 gtg tgc cag ctc ggc tcc gac acc gag ggc cgc acg gac gac gcg gtg      192
Val Cys Gln Leu Gly Ser Asp Thr Glu Gly Arg Thr Asp Asp Ala Val
 50                      55                      60 ctg cac acc ttc gag cct tcg gcg ccg cgc gtg cac ccg atc cac ccc      240
Leu His Thr Phe Glu Pro Ser Ala Pro Arg Val His Pro Ile His Pro
 65                  70                      75                  80 ggc tcc tac gtg cgc gtc gag cgc ggg ctc gac cag ccg ctg cgc gcg      288
Gly Ser Tyr Val Arg Val Glu Arg Gly Leu Asp Gln Pro Leu Arg Ala
                 85                      90                  95 ctc acg ctc gaa tgc tgg gtg cag gtg tgg agc ctg ggc acg cgc cag      336
Leu Thr Leu Glu Cys Trp Val Gln Val Trp Ser Leu Gly Thr Arg Gln
             100                     105                     110 agc gtg atc ggg cag ttc gac ctg ccg ggc gcc tgc ggc tac ggg ctc      384
Ser Val Ile Gly Gln Phe Asp Leu Pro Gly Ala Cys Gly Tyr Gly Leu
         115                     120                     125 ttc atc gac gag gac ggg cgc gcg gtg ttc cac ctg ggc gac ggc ggc      432
Phe Ile Asp Glu Asp Gly Arg Ala Val Phe His Leu Gly Asp Gly Gly
 130                     135                     140 gcc ttc cgc gcc gag ggg cag ctc tcg ggc ggt gcg ctg cag cct cgg      480
Ala Phe Arg Ala Glu Gly Gln Leu Ser Gly Gly Ala Leu Gln Pro Arg
145                     150                     155                 160 cgc tgg cac cac gtc gtc gcg aca tgg aac ggt agc gag acg gtg ctg      528
Arg Trp His His Val Val Ala Thr Trp Asn Gly Ser Glu Thr Val Leu
                 165                     170                     175 tgg ctc gac ggc gag gcc gtc gcg agc ggc cgc ttc gac ggc ccg ctg      576
Trp Leu Asp Gly Glu Ala Val Ala Ser Gly Arg Phe Asp Gly Pro Leu
             180                     185                     190 cag ccg gga cgc gcg ccg ctg cgc ctg ggc agc agc ggc atc gac ggc      624
Gln Pro Gly Arg Ala Pro Leu Arg Leu Gly Ser Ser Gly Ile Asp Gly
         195                     200                     205 ctg gcg gac gcg ttc ctc gag ggc gac atc gtc atg ccg gcg atc tat      672
Leu Ala Asp Ala Phe Leu Glu Gly Asp Ile Val Met Pro Ala Ile Tyr
 210                     215                     220 tcg cac gcg ctg cag gcc gac gag gtc aag gcc cgt ttc gcc gac cgc      720
Ser His Ala Leu Gln Ala Asp Glu Val Lys Ala Arg Phe Ala Asp Arg
225                     230                     235                 240 ggc ctg cac acg ccg cgc ggc cgt acc gtg ctc gcc tgc tgg ccg ctg      768
Gly Leu His Thr Pro Arg Gly Arg Thr Val Leu Ala Cys Trp Pro Leu
                 245                     250                     255 cgc gag gag cgc ggc gac gtg gtg gcc gat gcc agc ggc cac cag cgc      816
Arg Glu Glu Arg Gly Asp Val Val Ala Asp Ala Ser Gly His Gln Arg
             260                     265                     270 acc ggc cgc atc gtc aac cac ggc acc tgg atg atc gtc ggc ccc gcc      864
Thr Gly Arg Ile Val Asn His Gly Thr Trp Met Ile Val Gly Pro Ala
         275                     280                     285 ttc gag ccg cac cgg gtg aac gag ttc tcg gac gaa ggc tac gac ccg      912
Phe Glu Pro His Arg Val Asn Glu Phe Ser Asp Glu Gly Tyr Asp Pro
 290                     295                     300 ctg acg gac ccc acg cgc ggc cac ggc ctg cgc ctg gcg agc gac gac      960
Leu Thr Asp Pro Thr Arg Gly His Gly Leu Arg Leu Ala Ser Asp Asp
305                     310                     315                 320 ctc tac gac tgc cgc tgg ccc gag agc cat gcg ttc cgc atg ccg gcg     1008
Leu Tyr Asp Cys Arg Trp Pro Glu Ser His Ala Phe Arg Met Pro Ala
                 325                     330                     335 gat gcg aag tcg ggc gtg tac gtg ggc cgc gtg agc ttc ctg ctc gac     1056
```

```
                Asp Ala Lys Ser Gly Val Tyr Val Gly Arg Val Ser Phe Leu Leu Asp
                            340                 345                 350 ggc cgg agc gcc gaa tac gac atc acc ttc atc gtg cgc cgc gct gcg          1104
Gly Arg Ser Ala Glu Tyr Asp Ile Thr Phe Ile Val Arg Arg Ala Ala
            355                 360                 365 aac cgc gct ccc gcg ccc gtg ctg gtg ctg tgc gcc acc aac agc tgg          1152
Asn Arg Ala Pro Ala Pro Val Leu Val Leu Cys Ala Thr Asn Ser Trp
    370                 375                 380 ctg gcc tac gcg gcc acg ccc ttc gcg aag aac gtc gcg agc gac ccg          1200
Leu Ala Tyr Ala Ala Thr Pro Phe Ala Lys Asn Val Ala Ser Asp Pro
385                 390                 395                 400 gtg tgg ccg cgc cgt tcg gcc ggc ctg cag aac agc cac ccc gag gcg          1248
Val Trp Pro Arg Arg Ser Ala Gly Leu Gln Asn Ser His Pro Glu Ala
                405                 410                 415 ccg gcc ttc tgc agc tac acc tac cac cgc ggc ggc cag ccc acc tac          1296
Pro Ala Phe Cys Ser Tyr Thr Tyr His Arg Gly Gly Gln Pro Thr Tyr
            420                 425                 430 cag gtc ggc ctg cgc atg ccc tgg ccc aac gcc agc ccc aat gcg ctg          1344
Gln Val Gly Leu Arg Met Pro Trp Pro Asn Ala Ser Pro Asn Ala Leu
        435                 440                 445 tac gac ccg gcc gat gcc ggc ttc agc cag tgg aca cgg ctg gag cgc          1392
Tyr Asp Pro Ala Asp Ala Gly Phe Ser Gln Trp Thr Arg Leu Glu Arg
    450                 455                 460 cgc ctg cac gtg tgg ctc gat cgc tgc ggc tac gag tac gac gtg gtg          1440
Arg Leu His Val Trp Leu Asp Arg Cys Gly Tyr Glu Tyr Asp Val Val
465                 470                 475                 480 agc gac ctc gac ctg cac cgc gac ccg ggc ctg ctg aag gcc tac ggc          1488
Ser Asp Leu Asp Leu His Arg Asp Pro Gly Leu Leu Lys Ala Tyr Gly
                485                 490                 495 acg gtc ttc atc aat ggc cac agc gaa tac tgg tcg cag ccg gcc tgc          1536
Thr Val Phe Ile Asn Gly His Ser Glu Tyr Trp Ser Gln Pro Ala Cys
            500                 505                 510 gat ggg ctc gac gac tac ctg tcg aac ggc ggc acc gcc atc gtg ctg          1584
Asp Gly Leu Asp Asp Tyr Leu Ser Asn Gly Gly Thr Ala Ile Val Leu
        515                 520                 525 tcg ggc aac acc atg tac ctg cgc gtg agc tac gac gag gaa tgc acg          1632
Ser Gly Asn Thr Met Tyr Leu Arg Val Ser Tyr Asp Glu Glu Cys Thr
    530                 535                 540 gtg atg gag cag cgc aag gtg cgc ggc ccc ggc gac gag gac ggc gcc          1680
Val Met Glu Gln Arg Lys Val Arg Gly Pro Gly Asp Glu Asp Gly Ala
545                 550                 555                 560 gaa tcg gtg gag ctg cgc ccg ccg gcc ggc ccc tac ggc gag cag tac          1728
Glu Ser Val Glu Leu Arg Pro Pro Ala Gly Pro Tyr Gly Glu Gln Tyr
                565                 570                 575 cac tcg cag gac tgg gcg cgc ggc ggc cag ttc agg cag gcc ggg cgt          1776
His Ser Gln Asp Trp Ala Arg Gly Gly Gln Phe Arg Gln Ala Gly Arg
            580                 585                 590 tcg tgc gcc gac ctc atc gga ctg gag tcg gcc ggc tgg gcc ttc gcc          1824
Ser Cys Ala Asp Leu Ile Gly Leu Glu Ser Ala Gly Trp Ala Phe Ala
        595                 600                 605 gac ggc gac gac ttc ggc gtg tac cac gcg acg cag ccg ggg cac ttt          1872
Asp Gly Asp Asp Phe Gly Val Tyr His Ala Thr Gln Pro Gly His Phe
    610                 615                 620 ctg ttc acg cag ccg cat ccg ctg ggg ctc gaa gaa ggc tcc acc ttc          1920
Leu Phe Thr Gln Pro His Pro Leu Gly Leu Glu Glu Gly Ser Thr Phe
625                 630                 635                 640 ggc cat gcg ccg ggc ggt ggc ctg ccg agg gcc atc ggc cac gag tgg          1968
Gly His Ala Pro Gly Gly Gly Leu Pro Arg Ala Ile Gly His Glu Trp
                645                 650                 655
```

```
gac ctg agc gtg gcg acg ctg cgg cgc atg acg cgc acg ctg ccc gcg    2016
Asp Leu Ser Val Ala Thr Leu Arg Arg Met Thr Arg Thr Leu Pro Ala
            660                 665                 670 ggc gag cgc ctg ccc gag ccg cat cgc ggc atc cag gtc atc gcc gag    2064
Gly Glu Arg Leu Pro Glu Pro His Arg Gly Ile Gln Val Ile Ala Glu
675                 680                 685 ggg cgc agg cag cgc ccc ggg cgg ctc gac gcc tac ctc gac tac tac    2112
Gly Arg Arg Gln Arg Pro Gly Arg Leu Asp Ala Tyr Leu Asp Tyr Tyr
        690                 695                 700 tcg cag ccg acc gat tcg ctg ggc ggg cta tcg gcc gag atg atc tat    2160
Ser Gln Pro Thr Asp Ser Leu Gly Gly Leu Ser Ala Glu Met Ile Tyr
705                 710                 715                 720 tgg gag cgc ccg caa ggc ggc cgc gtg ttc aac gca ggc gcc gtc ggc    2208
Trp Glu Arg Pro Gln Gly Gly Arg Val Phe Asn Ala Gly Ala Val Gly
                725                 730                 735 gcg agc tgg gtg ctc ggc gcc gac ccc tca ttc gaa ggg ctg ctg cgc    2256
Ala Ser Trp Val Leu Gly Ala Asp Pro Ser Phe Glu Gly Leu Leu Arg
            740                 745                 750 aac gtg ctg cac cac ttc ggc gtc cgg ccc gcg acg ggc gcg gac ctt    2304
Asn Val Leu His His Phe Gly Val Arg Pro Ala Thr Gly Ala Asp Leu
        755                 760                 765 gca gat caa cca tcc ctg gag cac gca gca cca tga                    2340
Ala Asp Gln Pro Ser Leu Glu His Ala Ala Pro
770                 775

<210> SEQ ID NO 12
<211> LENGTH: 779
<212> TYPE: PRT
<213> ORGANISM: Variovorax sp. AJ110348

<400> SEQUENCE: 12

Met Thr Met Gln Gln Lys Ile Leu Pro Pro His Arg Ser Leu Gln
1               5                   10                  15

Val Pro Gly Val His Gly Tyr Thr Asp Arg Lys Ser Val Ala Ala Gly
            20                  25                  30

Glu Val Val Arg Phe His Ile Ser Ser Asp Val Pro Tyr Thr Leu Ser
        35                  40                  45

Val Cys Gln Leu Gly Ser Asp Thr Glu Gly Arg Thr Asp Asp Ala Val
    50                  55                  60

Leu His Thr Phe Glu Pro Ser Ala Pro Arg Val His Pro Ile His Pro
65                  70                  75                  80

Gly Ser Tyr Val Arg Val Glu Arg Gly Leu Asp Gln Pro Leu Arg Ala
                85                  90                  95

Leu Thr Leu Glu Cys Trp Val Gln Val Trp Ser Leu Gly Thr Arg Gln
            100                 105                 110

Ser Val Ile Gly Gln Phe Asp Leu Pro Gly Ala Cys Gly Tyr Gly Leu
        115                 120                 125

Phe Ile Asp Glu Asp Gly Arg Ala Val Phe His Leu Gly Asp Gly Gly
    130                 135                 140

Ala Phe Arg Ala Glu Gly Gln Leu Ser Gly Gly Ala Leu Gln Pro Arg
145                 150                 155                 160

Arg Trp His His Val Val Ala Thr Trp Asn Gly Ser Glu Thr Val Leu
                165                 170                 175

Trp Leu Asp Gly Glu Ala Val Ala Ser Gly Arg Phe Asp Gly Pro Leu
            180                 185                 190

Gln Pro Gly Arg Ala Pro Leu Arg Leu Gly Ser Ser Gly Ile Asp Gly
        195                 200                 205
```

-continued

```
Leu Ala Asp Ala Phe Leu Glu Gly Asp Ile Val Met Pro Ala Ile Tyr
    210                 215                 220

Ser His Ala Leu Gln Ala Asp Glu Val Lys Ala Arg Phe Ala Asp Arg
225                 230                 235                 240

Gly Leu His Thr Pro Arg Gly Arg Thr Val Leu Ala Cys Trp Pro Leu
                245                 250                 255

Arg Glu Glu Arg Gly Asp Val Val Ala Asp Ala Ser Gly His Gln Arg
                260                 265                 270

Thr Gly Arg Ile Val Asn His Gly Thr Trp Met Ile Val Gly Pro Ala
            275                 280                 285

Phe Glu Pro His Arg Val Asn Glu Phe Ser Asp Glu Gly Tyr Asp Pro
    290                 295                 300

Leu Thr Asp Pro Thr Arg Gly His Gly Leu Arg Leu Ala Ser Asp Asp
305                 310                 315                 320

Leu Tyr Asp Cys Arg Trp Pro Glu Ser His Ala Phe Arg Met Pro Ala
                325                 330                 335

Asp Ala Lys Ser Gly Val Tyr Val Gly Arg Val Ser Phe Leu Leu Asp
                340                 345                 350

Gly Arg Ser Ala Glu Tyr Asp Ile Thr Phe Ile Val Arg Arg Ala Ala
            355                 360                 365

Asn Arg Ala Pro Ala Pro Val Leu Val Leu Cys Ala Thr Asn Ser Trp
    370                 375                 380

Leu Ala Tyr Ala Ala Thr Pro Phe Ala Lys Asn Val Ala Ser Asp Pro
385                 390                 395                 400

Val Trp Pro Arg Arg Ser Ala Gly Leu Gln Asn Ser His Pro Glu Ala
                405                 410                 415

Pro Ala Phe Cys Ser Tyr Thr Tyr His Arg Gly Gly Gln Pro Thr Tyr
                420                 425                 430

Gln Val Gly Leu Arg Met Pro Trp Pro Asn Ala Ser Pro Asn Ala Leu
            435                 440                 445

Tyr Asp Pro Ala Asp Ala Gly Phe Ser Gln Trp Thr Arg Leu Glu Arg
    450                 455                 460

Arg Leu His Val Trp Leu Asp Arg Cys Gly Tyr Glu Tyr Asp Val Val
465                 470                 475                 480

Ser Asp Leu Asp Leu His Arg Asp Pro Gly Leu Leu Lys Ala Tyr Gly
                485                 490                 495

Thr Val Phe Ile Asn Gly His Ser Glu Tyr Trp Ser Gln Pro Ala Cys
                500                 505                 510

Asp Gly Leu Asp Asp Tyr Leu Ser Asn Gly Thr Ala Ile Val Leu
            515                 520                 525

Ser Gly Asn Thr Met Tyr Leu Arg Val Ser Tyr Asp Glu Glu Cys Thr
530                 535                 540

Val Met Glu Gln Arg Lys Val Arg Gly Pro Gly Asp Glu Asp Gly Ala
545                 550                 555                 560

Glu Ser Val Glu Leu Arg Pro Pro Ala Gly Pro Tyr Gly Glu Gln Tyr
                565                 570                 575

His Ser Gln Asp Trp Ala Arg Gly Gln Phe Arg Gln Ala Gly Arg
                580                 585                 590

Ser Cys Ala Asp Leu Ile Gly Leu Glu Ser Ala Gly Trp Ala Phe Ala
            595                 600                 605

Asp Gly Asp Asp Phe Gly Val Tyr His Ala Thr Gln Pro Gly His Phe
    610                 615                 620

Leu Phe Thr Gln Pro His Pro Leu Gly Leu Glu Glu Gly Ser Thr Phe
```

```
                        625                 630                 635                 640
Gly His Ala Pro Gly Gly Leu Pro Arg Ala Ile Gly His Glu Trp
                645                 650                 655
Asp Leu Ser Val Ala Thr Leu Arg Arg Met Thr Arg Thr Leu Pro Ala
            660                 665                 670
Gly Glu Arg Leu Pro Glu Pro His Arg Gly Ile Gln Val Ile Ala Glu
        675                 680                 685
Gly Arg Arg Gln Arg Pro Gly Arg Leu Asp Ala Tyr Leu Asp Tyr Tyr
    690                 695                 700
Ser Gln Pro Thr Asp Ser Leu Gly Gly Leu Ser Ala Glu Met Ile Tyr
705                 710                 715                 720
Trp Glu Arg Pro Gln Gly Gly Arg Val Phe Asn Ala Gly Ala Val Gly
                725                 730                 735
Ala Ser Trp Val Leu Gly Ala Asp Pro Ser Phe Glu Gly Leu Leu Arg
            740                 745                 750
Asn Val Leu His His Phe Gly Val Arg Pro Ala Thr Gly Ala Asp Leu
        755                 760                 765
Ala Asp Gln Pro Ser Leu Glu His Ala Ala Pro
    770                 775
```

```
<210> SEQ ID NO 13
<211> LENGTH: 31
<212> TYPE: DNA
<213> ORGANISM: Artificial Sequence
<220> FEATURE:
<223> OTHER INFORMATION: R 7F Primer

<400> SEQUENCE: 13
cgaggatccg cagcaggttc aggtcgatat c                               31

<210> SEQ ID NO 14
<211> LENGTH: 29
<212> TYPE: DNA
<213> ORGANISM: Artificial Sequence
<220> FEATURE:
<223> OTHER INFORMATION: R R HindIII Primer

<400> SEQUENCE: 14
cccaagcttt cagtcgacct cggtgtgag                                  29

<210> SEQ ID NO 15
<211> LENGTH: 30
<212> TYPE: DNA
<213> ORGANISM: Artificial Sequence
<220> FEATURE:
<223> OTHER INFORMATION: S F NdeI 2 Primer

<400> SEQUENCE: 15
tttctgccat atgaacgatc tcgcctcacg                                 30

<210> SEQ ID NO 16
<211> LENGTH: 29
<212> TYPE: DNA
<213> ORGANISM: Artificial Sequence
<220> FEATURE:
<223> OTHER INFORMATION: S R HindIII Primer

<400> SEQUENCE: 16
cccaagcttc gctagacgaa agtcagaag                                  29

<210> SEQ ID NO 17
```

```
<211> LENGTH: 30
<212> TYPE: DNA
<213> ORGANISM: Artificial Sequence
<220> FEATURE:
<223> OTHER INFORMATION: VRACY 1F NdeI Primer

<400> SEQUENCE: 17
ccaccgccat atgacgatgc agcagcagaa                                    30

<210> SEQ ID NO 18
<211> LENGTH: 30
<212> TYPE: DNA
<213> ORGANISM: Artificial Sequence
<220> FEATURE:
<223> OTHER INFORMATION: VRACY R HindIII Primer

<400> SEQUENCE: 18
gcgaaagctt tcatggtgct gcgtgctcca                                    30
```